(12) United States Patent
Herzinger et al.

(10) Patent No.: US 7,280,194 B1
(45) Date of Patent: Oct. 9, 2007

(54) ACCURATE DETERMINATION OF REFRACTIVE INDICES OF SOLID, FLUID AND LIQUID MATERIALS

(75) Inventors: Craig M. Herzinger, Lincoln, NE (US); Steven E. Green, Lincoln, NE (US); Gregory K. Pribil, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 431 days.

(21) Appl. No.: 11/000,490

(22) Filed: Nov. 30, 2004

(51) Int. Cl.
  *G01N 21/41* (2006.01)
(52) U.S. Cl. ............... 356/128; 356/135; 356/137
(58) Field of Classification Search ......... 356/128, 356/135
  See application file for complete search history.

(56) References Cited

U.S. PATENT DOCUMENTS

| | | | |
|---|---|---|---|
| 2,413,208 A | 12/1946 | Barnes | |
| 2,649,013 A | 8/1953 | Schnelle | |
| 2,649,014 A | 8/1953 | Johnsen | |
| 2,972,926 A | 2/1961 | Glodberg et al. | |
| 3,090,222 A | 5/1963 | Akaboshi | |
| 3,449,051 A | 6/1969 | Levitt | |
| 3,450,476 A | 6/1969 | Rando | |
| 3,797,940 A | 3/1974 | King ..................... | 356/134 |
| 4,284,352 A | 8/1981 | Carson et al. .............. | 356/134 |
| 4,286,873 A | 9/1981 | Carson ..................... | 356/130 |
| 4,381,895 A | 5/1983 | Hughes et al. .............. | 356/134 |
| 4,756,618 A | 7/1988 | Spry ........................ | 356/134 |
| 5,696,580 A | 12/1997 | Kubo et al. .................. | 356/72 |
| 6,549,276 B1 | 4/2003 | Longtin ..................... | 356/128 |

OTHER PUBLICATIONS

Demchuk, Vyu; Zaitsev, SU 1511647, Pub Date Sep. 30, 1989.*
"Refractive Index and Dispersion of Distilled Water for Visible Radiation, at Temperatures 0 to 60° Centigrade", Tilton et al., NIST, (1938).
"Revised Formulation for the Refractive Index of Water and Steam as a Function of Wavelength, Temperature ad Density", Harvey et al., J. Phys. Chem. Data, vol. 27, No. 4 (1998).
"Measurement of the Refractive Index of a Prism by a Critical Angle Method", Talim, Optica Acta, vol. 25, No. 2 (1978).
"Refractive-index Measurement of Bulk Materials: Prism Coupling Method", Onodera et al., Applied Optics, vol. 22, No. 8, (1983).
"Refractive Index of Liquid Solutions at Low Temperatures: An Accurate Measurement", Grange et al. Applied Optics, vol. 15, No. 4, (1976).
"Alternatives to the Minimum Deviation Method for Refractive Index Measurement", Dougal, Am. J. Phys. 54(4) (1996).
"A Simple, Accurate Alternative to the Minimum Deviation Method of Determining the Refractive Index of Liquids", Chandra et al. Am. J. Phys. 51(2), (1983).
"Absolute Refractive Indicies and Thermal Coefficients of Fused Silica and Calcium Fluoride Near 193 NM", Gupta et al., Applied Optics, vol. 37, No. 25, (1998).

(Continued)

*Primary Examiner*—Roy M. Punnoose
(74) *Attorney, Agent, or Firm*—James D. Welch

(57) ABSTRACT

Systems and methodology for determining not only precise and repeatable results, but accurate values of the refractive index of solids, fluids and liquids.

22 Claims, 9 Drawing Sheets

OTHER PUBLICATIONS

"Absolute Refractive Indicies and Thermal Coefficients of CaF2, SrF2, BaF2, and LiF Near 157 NM", Applied Optics, vol. 41, No. 13, (2002).

"Measurement of the Refractive Index and ThermopOptic Coefficient of Water Near 193 NM", Proc. SPIE, Optical Microlithography XVI, (2003).

"Immersion Fluid Refractive Indicies Using Prism Minimum Deviation Techniques", French et al., Proc. SPIE, vol. 5377, Op. Microlithography XVII, (2004).

"Immersion Fluids for Lithography: Refractive Index Measurement using Prism Minimum Deviation Techniques", Synowicki et al., Semiconductor Fabtech, 22nd Edition, Henely Publishing Ltd., London, UK.

"Refractometry by Minimum Deviation: Accuracy Analysis", Tentori et al., Op. Engineering, vol. 29, No. 2, Feb. (1980).

"Prism", Wolfram Science World, found at Website http://scienceworld.wolfram.com/physics/Prism.html.

\* cited by examiner

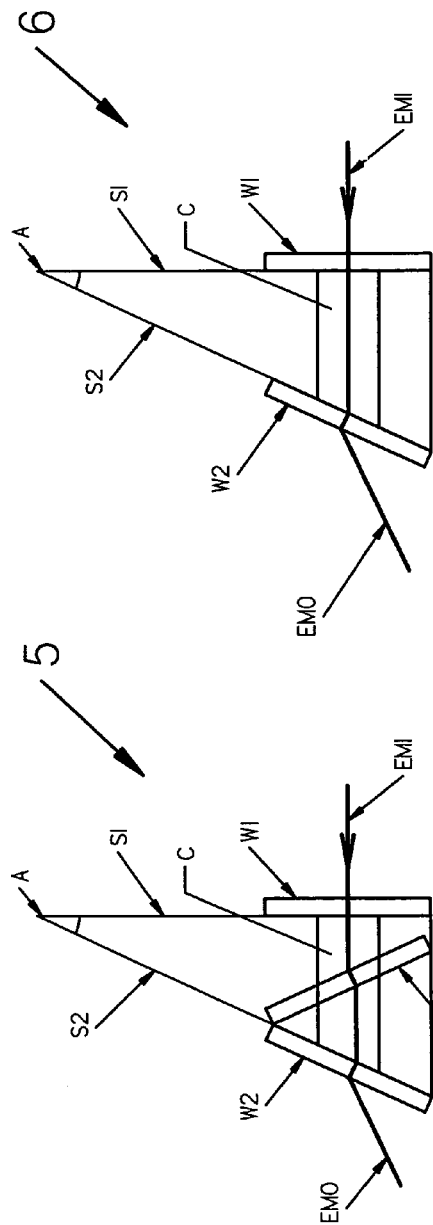
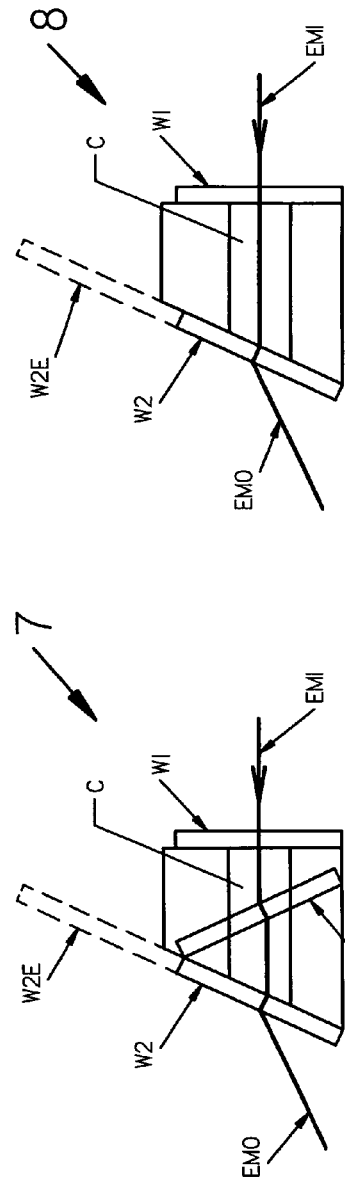
FIG-3E
FIG-3F
FIG-3G
FIG-3H

Deviation vs. Angle of Incidence

ACCURATE DETERMINATION OF REFRACTIVE INDICES OF SOLID, FLUID AND LIQUID MATERIALS

TECHNICAL FIELD

The disclosed invention relates to determination of refractive indices of materials, and more particularly to systems and methodology for determining not only precise and repeatable results, but accurate values of the refractive index of solids, fluids and liquids.

BACKGROUND

As semiconductor device dimensions decrease, the need to perform lithography at shorter wavelengths becomes more critical. One method of simulating the results achievable by direct application of short wavelengths, is to apply longer wavelengths through refractive liquid. Accurate determination of the refractive index of liquids to be applied in said simulated shorter wavelength lithography then becomes critical.

A well known technique for determining the refractive index of a material is to provide a triangular shaped prism of the material, mount it to a front of a rotatable stage, provide a beam of electromagnetic radiation which is directed to impinge upon one side thereof, and further provide a pivot mounted detector which is positionable to intercept the beam of electromagnetic radiation which exits said triangular shaped prism. This can be visualized in elevation where the rotatable stage is pivotally mounted to a horizontally projected axile means about which said rotatable stage can be caused to rotate, (eg. a projecting rod), which extends from a vertically oriented support. The source of electromagnetic radiation can be envisioned as fixedly mounted to the right (left) of said rotatably mounted stage with the detector mounted to the left (right) via an arm which is pivotally mounted at the location of the horizontally projected means about which said rotatable stage can be caused to rotate, to which is pivotally mounted at said rotatable stage. Note, the described orientation of the system is exemplary only, and the entire system can be rotated to orient the horizontally projected axile means about which said rotatable stage rotates vertically, so that the front of the stage faces vertically, or for that matter, oriented in any functional direction. Of course it is assumed that the Source of electromagnetic radiation and stage front and detector stay relatively in the same orientation with respect to said projected projected axile means during any such rotation.

Known Article references are:

"Refractive Index and Dispersion of Distilled Water for Visible Radiation, at Temperatures 0 to 60° Centigrade", Tilton et al., NIST, (1938).

"Revised Formulation for the Refractive Index of Water and Steam as a Function of Wavelength, Temperature ad Density", Harvey et al., J. Phys. Chem. Data, Vol. 27, No. 4 (1998).

"Measurement of the Refractive Index of a Prism by a Critical Angle Method", Talim, Optica Acta, Vol. 25, No. 2 (1978).

"Refractive-index Measurement of Bulk Materials: Prism Coupling Method", Onodera et al., Applied Optics, Vol. 22, No. 8, (1983).

"Refractive Index of Liquid Solutions at Low Temperatures: An Accurate Measurement", Grange et al. Applied Optics, Vol. 15, No. 4, (1976).

"Alternatives to the Minimum Deviation Method for Refractive Index Measurement", Dougal, Am. J. Phys. 54(4) (1996).

"A Simple, Accurate Alternative to the Minimum Deviation Method of Determining the Refractive Index of Liquids", Chandra et al. Am. J. Phys. 51(2), (1983).

"Absolute Refractive Indicies and Thermal Coefficients of Fused Silica and Calcium Fluoride Near 193 NM", Gupta et al., Applied Optics, Vol. 37, No. 25, (1998).

"Absolute Refractive Indicies and Thermal Coefficients of CaF2, SrF2, BaF2, and LiF Near 157 NM", Applied Optics, Vol. 41, No. 13, (2002).

"Measurement of the Refractive Index and ThermopOptic Coefficient of Water Near 193 NM", Proc. SPIE, Optical Microlithography XVI, (2003).

"Immersion Fluid Refractive Indicies Using Prism Minimum Deviation Techniques", French et al., Proc. SPIE, Vol. 5377, Op. Microlithography XVII, (2004).

"Immersion Fluids for Lithography: Refractive Index Measurement using Prism Minimum Deviation Techniques", Synowicki et al., Semiconductor Fabtech, 22nd Edition, Henely Publishing Ltd., London, UK.

"Refractometry by Minimum Deviation: Accuracy Analysis", Tentori et al., Op. Engineering, Vol. 29, No. 2, February (1980).

"Prism", Wolfram Science World, found at Website http://scienceworld.wolfram.com/physics/Prism.html.

A Search of patents which describe apparatus and methodology which can be applied to a similar end as taught in this Application has provided:

U.S. Pat. No. 4,756,618 to Spry;
U.S. Pat. No. 3,797,940 to King;
U.S. Pat. No. 3,450,476 to Rando;
U.S. Pat. No. 3,090,222 to Akabosch et al.;
U.S. Pat. No. 2,649,014 to Johnsen;
U.S. Pat. No. 2,649,013 to Schnelle;
U.S. Pat. No. 5,696,580 to Kubo et al.;
U.S. Pat. No. 4,381,895 to Hughes et al.;
U.S. Pat. No. 6,549,276 to Longtin;
U.S. Pat. No. 4,286,873 to Carson;
U.S. Pat. No. 4,284,352 to Carson et al.;
U.S. Pat. No. 3,449,051 to Levitt;
U.S. Pat. No. 2,972,926 to Goldberg et al.;
U.S. Pat. No. 2,413,208 to Barnes.

Need remains for apparatus and methodology of its application in the area of determining optical properties of fluids and in particular, liquids.

DISCLOSURE OF THE INVENTION

One primary embodiment of the disclosed invention provides that a triangular shaped prism be positioned on a rotatably mounted stage, and that a beam of electromagnetic radiation from a source thereof be caused to impinge upon one side of said triangular shaped prism. The rotatable stage is then caused to be stepped through a sequence of rotation angles, and at each thereof the detector is caused to be rotated about the pivot mounting of the arm to which it is attached, while intensity measurements are taken at a sequence of said detector angular positions. For each position of the rotatable stage, said detected intensity measurements as a function of detector position, are found to peak. Said peaks are identifying of "Deviation Angle" of the electromagnetic beam caused by its passage through said prism material. When a plot of "Deviation Angle" vs. Angle-of-Incidence of the electromagnetic beam with respect to a normal to the side of the triangular shaped prism onto which it impinges, it is found to demonstrate a Minimum. If the electromagnetic beam impinged at the Apex of the triangular shaped prism and said Apex were affixed to the rotatable stage at the location of the horizontally projecting rod, such would be the True Minimum Deviation Angle. However, since it is impractical to direct the electromagnetic beam at said Apex, (especially where liquid is to be contained within a cavity in the Triangular shape prism), and as the electromagnetic beam is typically caused to impinge on the triangular shaped prism at a location removed therefrom, said measured/observed Minimum is not a True Minimum Deviation. (Note, while this Disclosure, in some embodiments, refers to use of a Rotable Stage. It is of course possible to, alternatively or in supplement to a Stage motion, move the location of the Source of the electromagnetic beam to achieve the same result. For the purposes of this Disclosure, unless otherwise specifically stated, the terminology "Stage Rotation" is to be read to include a functionally equivalent movement of the Source of the electromagnetic beam. That is, it is functionally the relative orientation of the Prism and electromagnetic beam which is of importance).

Continuing, even if the triangular shaped prism is mounted to the rotatable stage such that a projected locus of the horizontally projected rod to which the rotatable stage is attached, intersects the projected bisector of the Apex angle of the Triangular Shaped Prism, it is found that measured/observed Deviation Angle vs. Angle of Incidence data varies with the distance from said Apex, of the intersection of a projection of the locus of said projecting rod along the projected apex bisector, which defines a center of rotation. It is also found that if two sets of data taken with the triangular shaped prism positioned on the rotatable stage such that the projected apex bisector is intersected by the projected locus of the axile means for allowing stage rotation (eg. rod) at two (or more), different distances from the Apex, said sets of data, if plotted on the same graph of Deviation Angle vs. Angle of Incidence, intersect. (It is noted that identification of said intersection point can be determined by fitting mathematical function to the data and mathematically determining their intersection point). Said intersection point is identifying of the Angle-of-Incidence at which the true Minimum Deviation Angle occurs. Importantly, said Minimum Deviation Angle identifying Angle-of-Incidence is the Angle-of-Incidence at which an accurate Refractive Index can be obtained utilizing methodology of the disclosed invention. (See the Detailed description for a better disclosure of the relationship between the Angle-of-Incidence and the Deviation angle).

It is also noted that said triangular shaped prism can be positioned offset on said rotatable stage such that the projected apex bisector of said prism is not intersected by a projected locus of said rod about which the rotatable stage rotates. This can also enter error into accurate determination of Refractive Index of a material. Thus it is necessary to assure that a Triangular Prism is aligned on a rotatable stage such that a projection of the locus of the rod intersects the projected apex bisector, or correct for the offset. This can be accomplished by, for each of a plurality of "lateral" positions of said prism on said rotatable stage, which "lateral" positions are offset from one another along a perpendicular to the projected apex bisector of said prism, obtaining data corresponding to a plurality of rotation positions of said stage about said rod, (ie. axile means for allowing stage rotation), about which the stage rotates. Said data is obtained by causing an electromagnetic beam from said source of electromagnetic radiation to enter the first side prism at an angle of incidence to a normal to the plane of said first side of said prism, and at each angle of incidence, obtaining electromagnetic radiation peak intensity data for each of a plurality of detector position pivot angles, such that the detector position pivot angle at which the peak of the electromagnetic radiation intensity is detected is identified. Assuming said lateral offset of the locus of the projected rod is not too far removed from the projected apex bisector, (it is noted that eye-ball positioning of the prism is sufficient to provide a good result), peak intensity plot data provides information which allows determining any offset. Electromagnetic radiation peak Intensity vs. Angle of Incidence of said electromagnetic radiation beam to a normal to the plane of said first side of said prism can be inspected to demonstrate first and second slopes. If a data plot slope provides a peak at which the slope is zero (0.0), it corresponds to a correct positioning of the prism's projected apex bisector. If slopes are non-zero, the values of said slopes provide information which can be applied to calculate "lateral" positioning of said prism along a locus perpendicular to the projected apex bisector of said prism on said rotatable stage to position said prism such that its projected apex bisector intersects the projected locus of said the rod axile means for allowing stage rotation. It is also possible to simply effectively plot multiple plots of said peak electromagnetic radiation peak intensity data vs. Angle of Incidence on the same set of axes such that the "lateral" offset position of said prism on said rotatable stage associated with the highest electromagnetic radiation peak intensity can be identified. Around the Angle of Incidence whereat the effective minimum deviation angle occurres, said "lateral" position associated with the highest electromagnetic radiation intensity peak is identifying of the location of whereat the projected apex bisector of said prism is intersected by said projected locus of said the axile means for allowing stage rotation.

Any functional prism system can be applied in the methodology of he present invention method of determining Accurate Refractive Indices of materials. Some are simply made of solid material and some have provision for entry of liquid or fluid thereinto. Some suitable prism systems are described directly.

A first (1) system is a triangular prism having a projected apex bisector and first and second sides oriented at angles thereto which meet at the apex; such that in use a beam of electromagnetism is caused to enter said triangular shaped prism at the first side thereof along a locus in a plane parallel to said stage plane and at an angle of incidence to a normal to said first side, pass through said triangular shaped prism, and exit the second side of said triangular prism at an exit angle at least partially determined by the refractive index of the material comprising said triangular shaped prism.

A second (2) system is a triangular prism having a projected apex bisector and first and second sides oriented at angles thereto which meet at the apex; there being a cavity within said triangular and means for entering liquid/fluid thereinto, said cavity being bounded internally by a first and second windows oriented parallel to said first and second sides of said triangular prism respectively; such that in use liquid/fluid is caused to be present in said cavity, and a beam of electromagnetism is caused to enter said cavity at the first side of said triangular prism along a locus in a plane parallel to said stage plane and at an angle of incidence to a normal to said first side, pass through said first window, then through said liquid/fluid, then through said second window and exit the second side of said triangular prism at an exit angle at least partially determined by the refractive index of said liquid/fluid;

A third (3) system is a trapazoidal prism having a projected virtual apex bisector and first and second sides oriented at angles thereto which meet at a virtual apex; such that in use a beam of electromagnetism is caused to enter said trapezoidal prism at the first side of said triangular prism along a locus in a plane parallel to said stage plane, pass through said trapazoidal prism, and exit the second side of said triangular prism at an exit angle at least partially determined by the refractive index of the material comprising said trapazoidal shaped prism;

A fourth (4) system is a trapazoidal prism having a projected virtual apex bisector and first and second sides oriented at angles thereto which meet at the virtual apex; there being a cavity within said trapazoidal prism and means for entering liquid/fluid thereinto, said cavity being bounded internally by first and second windows oriented parallel to said first and second sides of said trapazoidal prism respectively; such that in use liquid/fluid is caused to be present in said cavity, and a beam of electromagnetism is caused to enter said cavity at the first side of said trapazoidal prism along a locus in a plane parallel to said stage plane and at an angle of incidence to a normal to said first side, pass through said first window, then through said liquid/fluid, then through said second window and exit the second side of said trapazoidal prism at an exit angle at least partially determined by the refractive index of said liquid/fluid.

A fifth (5) system for use in accurately determining the refractive index of liquid/fluid is a triangular half-prism comprising, as viewed in side elevation, a first side which meets a second side oriented at an angle to said first side, at an apex; there being a cavity within said triangular half-prism and means for entering liquid/fluid thereinto, said cavity being bounded internally by a first window oriented parallel to said first side of said triangular half-prism, a second window oriented parallel to said second side of said triangular half-prism and, between said first and second sides of said triangular half-prism inside said cavity, there being a third window which is oriented parallel to a mirror image of said second window taken about said first side of said triangular half-prism; such that in use liquid/fluid is caused to be present in said cavity, and a beam of electromagnetism is caused to enter said cavity through said first window at the first side of said triangular half-prism along a locus parallel to said stage plane and perpendicular to said first window, pass sequentially through liquid/fluid, said third window, liquid/fluid, and then through said second window and exit the second side of said triangular half-prism at an exit angle at least partially determined by the refractive index of said liquid/fluid.

A sixth (6) system for use in accurately determining the refractive index of liquid/fluid is a triangular half-prism comprising, as viewed in side elevation, a first side which meets a second side oriented at an angle to said first side, at an apex; there being a cavity within said triangular half-prism and means for entering liquid/fluid thereinto, said cavity being bounded internally by a first window oriented parallel to said first side of said triangular half-prism, a second window oriented parallel to said second side of said triangular half-prism and; such that in use liquid/fluid is caused to be present in said cavity, and a beam of electromagnetism is caused to enter said cavity through said first window at the first side of said triangular half-prism along a locus parallel to said stage plane and perpendicular to said first window, pass sequentially through liquid/fluid and then through said second window and exit the second side of said triangular half-prism at an exit angle at least partially determined by the refractive index of said liquid/fluid.

A seventh (7) system for use in accurately determining the refractive index of liquid/fluid is a trapazoidal half-prism comprising, as viewed in side elevation, a first side which meets a second side oriented at an angle to said first side, at a virtual apex; there being a cavity within said trapazoidal half-prism and means for entering liquid/fluid thereinto, said cavity being bounded internally by a first window oriented parallel to said first side of said trapazoidal half-prism, a second window oriented parallel to said second side of said trapazoidal half-prism and, between said first and second sides of said trapazoidal half-prism inside said cavity, there being a third window which is oriented parallel to a mirror image of said second window taken about said first side of said trapazoidal half-prism; such that in use liquid/fluid is caused to be present in said cavity, and a beam of electromagnetism is caused to enter said cavity through said first window at the first side of said trapazoidal half-prism along a locus parallel to said stage plane and perpendicular to said first window, pass sequentially through liquid/fluid, said third window, liquid/fluid, and then through said second window and exit the second side of said triangular half-prism at an exit angle at least partially determined by the refractive index of said liquid/fluid;

An eighth (8) system for use in accurately determining the refractive index of liquid/fluid is a trapazoidal half-prism comprising, as viewed in side elevation, a first side which meets a second side oriented at an angle to said first side, at a virtual apex; there being a cavity within said trapazoidal half-prism and means for entering liquid/fluid thereinto, said cavity being bounded internally by a first window oriented parallel to said first side of said trapazoidal half-prism, a second window oriented parallel to said second side of said trapazoidal half-prism and; such that in use liquid/fluid is caused to be present in said cavity, and a beam of electromagnetism is caused to enter said cavity through said first window at the first side of said trapazoidal half-prism along a locus parallel to said stage plane and perpendicular to said first window, pass sequentially through liquid/fluid and then through said second window and exit the second side of said triangular half-prism at an exit angle at least partially determined by the refractive index of said liquid/fluid.

It is noted that in Systems 2, 4 and 5-8 can have an elongated second window projected beyond the prism per se., (ie. it projects beyond the extent of the second side in any functional direction), for use in alignment and accurate determination of the angle at which the first and second sides meet at the apex or virtual apex. In use the prism can be positioned on the stage such that an electromagnetic beam from the source thereof reflects directly back from said elongated second window, and then the prism is positioned and rotated and so that said electromagnetic beam from the source thereof reflects directly back from said first window. The angle of rotation is the angle at which the first and second sides meet at the apex or virtual apex. Note that one side of the elongated portion of the second window is typically frosted or roughened or otherwise made to be non-reflective, and again, the reflective projection of said second window can be in any direction beyond the prism per se. Preferred practice is to have it project out of or into a page upon which the prism is shown in side elevation. However, the projection direction of the elongated second window can also be upward toward the virtual apex where a trapazoidal prism is utilized.

It is also noted that one approach of determining that a beam of electromagnetic radiation approaches and reflects directly back from a surface, is to pass said beam through a central hole in a quad detector such that it then reflects from said surface, and monitor reflected input to the quad detector detector elements. Ideally all detector elements will show zero output, but if the beam spreads so that electromagnetic radiation does enter the detector elements, proper alignment is where the outputs are substantially equal.

A method of improving accuracy in determining the refractive index of material or liquid/fluid can then be described as comprising the steps of:

a) providing a system comprising:
   a structure;
   a source of electromagnetic radiation;
   a rotatable stage; and
   a detector;

said rotatable stage having a front side which is defining of a stage plane, and being rotatably mounted to said structure at an axile means for allowing stage rotation thereabout, about which axile means said rotatable stage can be caused to rotate in said stage plane; said source of electromagnetic radiation being fixed in location at an offset from said rotatable stage, and said detector being attached to an arm which is pivotally secured to said structure at the location of said rotatable stage;

the relative positioning of said source of electromagnetic radiation, rotatable stage and detector being such that a beam of electromagnetic radiation produced by said source thereof can be directed to proceed in a plane parallel to, but offset from, the stage plane, and enter said detector when it is positioned at a detector pivot angle which allows receipt of said beam of electromagnetic radiation, said pivot angle being effected by pivot motion of said arm which is pivotally secured to said structure the location of said rotatable stage;

b) placing a prism on the front side of said rotatable stage, said prism being a selection from the group consisting of one of the systems identified as System 1, 2, 3, and 4 above; said selected prism being positioned on said rotatable stage such that projected apex bisector thereof is intersected by a projected locus of said the axile means for allowing stage rotation, at a first distance removed from said apex or virtual apex;

c) for each of a plurality of rotation positions of said stage about said axile means for allowing stage rotation thereabout, causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles such that the detector position pivot angle at which peak electromagnetic radiation intensity is detected is identified;

d) providing an effective plot of a deviation angle determined from said detector position pivot angles at which peak electromagnetic radiation peak intensity is present vs. the angle of incidence of said beam of electromagnetic radiation to the normal to said first side of said prism, which plot demonstrates a minimum;

e) moving the selected prism on said stage such that it becomes positioned on said rotatable stage such that projected apex bisector thereof is intersected by a projected locus of said the axile means for allowing stage rotation, at a second distance removed from said apex or virtual apex, and repeating steps c and d;

f) locating intersection of the effective plots determined in the first and second practice of step d, and the minimum deviation angle identifying angle of incidence of the electromagnetic beam with respect to a normal to the plane of said first side of said prism, at said intersection;

g) utilizing data obtained at the angle of incidence and corresponding minimum deviation angle identified in step f in calculations to determine an accurate index of refraction for the material or liquid/fluid.

Another step, in the case where a System identified in 2 or 4 above is utilized and liquid/fluid is investigated, can involve effectively repeating the method without the liquid/fluid present inside the cavity and with the prism oriented to allow electromagnetic radiation to pass straight-through, to determine base line effects of the Prism System. This allows determination of any non-parallelism effects of the Windows. Said baseline effects can then be subtracted from the data obtained when liquid/fluid is present to further improve accuracy in determining Refractive index.

Another step, in the case where a System identified as System 2 or 4 above is utilized and liquid/fluid is investigated, can involve effectively repeating the method with a standard liquid/fluid present inside the cavity to determine base line effects of the Prism System. Comparison with published data for said standard liquid/fluid can identify effects which can then be subtracted from the data obtained when sample liquid/fluid is present, to further improve accuracy in determining Refractive index. Measurements using the standard liquid/fluid can also help determine when proper alignment of the prism has been achieved, with said proper alignment then being utilized when measuring sample liquid/fluid.

Said method of improving accuracy in determining the refractive index of material or liquid/fluid can further comprise assuring that said selected prism is positioned on said rotatable stage such that projected apex bisector of said prism is intersected a projected locus of said the axile means for allowing stage rotation, at one or more (eg. at first and second distance removed from said apex or virtual apex in steps a and e), said steps comprising:

a1) for each of at least two "lateral" positions of said prism on said rotatable stage, which "lateral" positions are offset from one another along a perpendicular to the projected apex bisector of said prism, obtaining data corresponding to a plurality of rotation positions of said stage about said axile means for allowing stage rotation thereabout, said data being obtained by causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles;

a2) identifying first and second slopes of effective plots of peak electromagnetic radiation peak intensity vs. angle of incidence of said electromagnetic radiation beam to a normal to the plane of said first side of said prism, corresponding to said two lateral positions of said prism on said rotatable stage;

a3) applying said first and second slopes determined in step a2) to calculate "lateral" positioning of said prism along a locus perpendicular to the projected apex bisector of said prism on said rotatable stage to position said prism such that its projected apex bisector intersects the a projected locus of said the axile means for allowing stage rotation, or to derive a correction factor for application to data obtained with the prism positioned other than with the prism projected apex bisector being intersected a projected locus of said the axile means for allowing stage rotation.

It is noted that the just recited method is not limited to use of only two, (ie. first and second), slopes, and that slope(s) of only one, or additional, (eg. more than two), effective plots can be applied as well.

Another approach to assuring that said selected prism is positioned on said rotatable stage such that projected apex bisector of said prism is intersected a projected locus of said the axile means for allowing stage rotation, at one or more, (eg. at first and second distance removed from said apex or virtual apex in steps a and e), said steps comprising:

a1) for each of a plurality of "lateral" positions of said prism on said rotatable stage, which "lateral" positions are offset from one another along a perpendicular to the projected apex bisector of said prism, obtaining data corresponding to a plurality of rotation positions of said stage about said axile means for allowing stage rotation thereabout, said data being obtained by causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles such that the detector position pivot angle at which peak electromagnetic radiation intensity is detected is identified;

a2) effectively plotting at least some of said plots of said peak electromagnetic radiation peak intensity data vs. angle of incidence obtained in step a1, on the same set of axes such that the "lateral" offset position of said prism on said rotatable stage associated with the highest electromagnetic radiation intensity can be identified, said "lateral" position associated with the highest electromagnetic radiation peak, (around the angle of incidence where the effective minimum deviation angle occurs), intensity being identifying of the location of whereat the projected apex bisector of said prism is intersected by said projected locus of said the axile means for allowing stage rotation, and applying said information to direct positioning of said prism on said stage rotatable stage so that the prism projected apex bisector intersects a projected locus of said the axile means for allowing stage rotation, or to derive a correction factor for application to data obtained with the prism positioned other than with the prism projected apex bisector being intersected a projected locus of said the axile means for allowing stage rotation.

It is, of course, possible to utilize both the first and second slopes, and highest electromagnetic radiation Intensity peaks in determining if a Prism is not aligned on a rotatable stage with its projected apex bisector intersected by a projected locus of the rod, (eg. axile means for allowing stage rotation), about which the rotatable stage rotates. It is noted that in all said lateral position determining steps, it is beneficial to obtain data corresponding to lateral offsets which are not too far removed from the condition whereat the prism projected apex bisector intersects a projected locus of said the axile means for allowing stage rotation. Eyeball positioning of the prism on the rotatable stage has been found sufficient to provide good starting values.

It is noted that an Alternative approach to compensating lateral offset from said Bisector of the Apex or Virtual Apexisector is to obtain data with a Prism in a first orientation, and then obtain data with the Prism rotated 180 degrees. A "Zone-Averaging" technique can then be applied to the two data sets, corresponding data point pair by corresponding data point pair, which results in a compensation of the lateral offset.

Another method of improving accuracy in determining the refractive index of material or liquid/fluid can then be described as comprising the steps of:

a) providing a system comprising:

a structure;

a source of electromagnetic radiation;

a rotatable stage; and a detector;

said rotatable stage having a front side which is defining of a stage plane, and being rotatably mounted to said structure at an axile means for allowing stage rotation thereabout, about which axile means said rotatable stage can be caused to rotate in said stage plane; said source of electromagnetic radiation being fixed in location at an offset from said rotatable stage, and said detector being attached to an arm which is pivotally secured to said structure the location of said rotatable stage;

the relative positioning of said source of electromagnetic radiation, rotatable stage and detector being such that a beam of electromagnetic radiation produced by said source thereof can be directed to proceed in a plane parallel to, but offset from, the stage plane, and enter said detector when it is positioned at a detector pivot angle which allows receipt of said beam of electromagnetic radiation, said pivot angle being effected by pivot motion of said arm which is pivotally secured to said structure the location of said rotatable stage;

b) placing a prism on the front side of said rotatable stage, said prism being a selection from the group consisting of one of the systems identified as System 1, 2, 3, and 4 above; said selected prism being positioned on said rotatable stage such that projected apex bisector thereof is intersected by a projected locus of said the axile means for allowing stage rotation, at a first distance removed from said apex or virtual apex;

c) for each of a plurality of rotation positions of said stage about said axile means for allowing stage rotation thereabout, causing an electromagnetic beam from said source of electromagnetic radiation to enter the first side or first window of said prism at an angle of incidence to a normal to the plane of said first side of said prism, and obtaining electromagnetic radiation intensity data for each of a plurality of detector position pivot angles such that the detector position pivot angle at which peak electromagnetic radiation intensity is detected is identified;

d) providing an effective plot of a deviation angle determined from said detector position pivot angles at which peak electromagnetic radiation peak intensity is present vs. the angle of incidence of said beam of electromagnetic radiation to the normal to said first side of said prism, which plot demonstrates a minimum;

e) in combination with determining the distance from the prism apex at which the projected apex bisector thereof is intersected by a projected locus of said the axile means for allowing stage rotation, and with determining the length along the arm which is pivotally secured to said structure the location of said rotatable stage, at which the detector is located, utilizing data obtained at the angle of incidence and corresponding minimum deviation angle identified in step d in calculations to determine an accurate index of refraction for the material or liquid/fluid.

It is noted that in the just recited method that the measurement is performed at only one location along the projected bisector. However, the location of intersection of the projected locus of the axile means for allowing stage rotation with respect to the apex bisector must be identified. As the Detector supporting arm which is pivotally secured to said structure the location of said rotatable stage has the same center of rotation, however, it can be substituted.

The foregoing embodiments require a rotatable stage, (and/or position adjustable Source of a beam of electromagnetic radiation). Some embodiments, however, leave as optional the use of a rotatable stage. In that light, another method of improving accuracy in determining the refractive index of material or liquid/fluid comprising the steps of:

a) providing a system comprising:
 a structure;
 a source of electromagnetic radiation;
 a stage; and
 a detector;

said stage having a front side which is defining of a stage plane, said source of electromagnetic radiation being fixed in location at an offset from said stage, and said detector being attached to an arm which is pivotally secured to said structure the location of said stage;

the relative positioning of said source of electromagnetic radiation, stage and detector being such that a beam of electromagnetic radiation produced by said source thereof can be directed to proceed in a plane parallel to, but offset from, the stage plane, and enter said detector when it is positioned at a detector pivot angle which allows receipt of said beam of electromagnetic radiation, said pivot angle being effected by pivot motion of said arm which is pivotally secured to said structure the location of said stage;

b) providing a prism selected from the group consisting of one of the systems identified as System 5, 6, 7 or 8 above on the front side of said stage;

c) causing an electromagnetic beam from said source of electromagnetic radiation to enter the first window of said prism at a angle of incidence to a normal to the plane of said first side of said prism, and obtaining electromagnetic radiation intensity data for each of a plurality of detector position pivot angles such that the detector position pivot angle at which peak electromagnetic radiation intensity is detected is identified;

d) utilizing data obtained in calculations to determine an accurate index of refraction for the material or liquid/fluid, or utilizing data obtained.

Another step, in the case where a System identified as System 2, 4, 5, 6, 7 or 8 above is utilized and liquid/fluid is investigated can involve effectively repeating the method without the liquid/fluid present inside the cavity and with the prism oriented to allow electromagnetic radiation to pass straight-through, to determine base line effects of the Prism System. This allows determination of any non-parallelism effects of the Windows. Said baseline effects can then be subtracted from the data obtained when liquid/fluid is present to further improve accuracy in determining Refractive index.

Another step, in the case where a System identified as System 2, 4, 5, 6, 7 or 8 above is utilized and liquid/fluid is investigated, can involve effectively repeating the method with a standard liquid/fluid present inside the cavity to determine base line effects of the Prism System. Comparison with published data for said standard liquid/fluid can identify effects which can then be subtracted from the data obtained when sample liquid/fluid is present, to further improve accuracy in determining Refractive index. Measurements using the standard liquid/fluid can also help determine when proper alignment of the prism has been achieved, with said proper alignment then being utilized when measuring sample liquid/fluid.

Another step, in the case where any System identified as 1-8 above, is utilized can comprise determination of the alignment of said source of electromagnetic radiation and detector by, without any prism or stage being present in the electromagnetic radiation beam path, causing electromagnetic radiation from said source thereof to directly enter said detector, and using any offset in alignment to correct determined refractive index.

It should further be appreciated that where two sets of data are taken, and have as a distinguishing factor different path lengths of path of the electromagnetic radiation beam through the prism, said two sets of data can be applied to determine absorption of the material or liquid/fluid, hence the Extinction Coefficient as well as the Refractive Index. This could be accomplished using Prisms 1-8 where measurements are acquired at two or more locations along the Projected Apex Bisector.

It is also noted that where a "Peak" is to be determined in a data set, one approach is to fit the data with a Mathematical Model which demonstrates a "Peak", such as well exemplified by a Gaussian Function. The "peak" is where the First Derivative is Zero, and the Second Derivative is Negative. Similarly, the "Minimum" of a Minimum Deviation Angle curve vs. Angle of Incidence can also be determined by fitting data with a Mathematical Model such as a Gaussian Function. At said Minimum the First Derivative is again Zero, and the Second Derivative is Positive.

It is to be understood that the Terminology "Effective Plots" should be interpreted to mean that where data is plotted for visual observation, one locus on a graph can be observed to, for instance, intersect another. However, said data need not be actually plotted to enable visual observation. Mathematical techniques can be applied to arrive at a solution to the intersection point. Thus the terminology "Effective Plot".

Further, for purposes of this Specification, the Terminology "Fluid" is to be considered equivalent to "Liquid", in the sense that the fluid or liquid/fluid can be flowed into a cavity similarly.

It is also noted that the disclosed system can be present in an environmental control chamber where wavelengths utilized are absorbed by oxygen and/or water vapor, (eg. in the VUV range below about 190 NM), or simply be located in open atmosphere where, for instance, visible range wavelengths are used.

Additionally, the rotation of the rotatable stage can be effected by a Theta-2-Theta angle-of-incidence goniometer stage, which can be manually operated or computer controlled by, for instance, via a stepper motor. And, it is also noted that where an AOI is indicated with respect to a Normal, said language is to be interpreted to include a Normal Angle of Incidence where functional, and where the terminology "Apex" is utilized "Virtual Apex" is to be considered as included therewithin, again where functional Finally, it is to be understood that the electromagnetic radiation can be unpolarized, partially polarized or polarized. Such polarized states can be imposed on electromagnetic radiation by reflectometer, ellipsometer and polarimeter systems.

BRIEF DESCRIPTION OF THE DRAWINGS

FIGS. 3a-3h disclose exemplarly, non-limiting, prism designs providing windows on the outside thereof.

DETAILED DESCRIPTION

Figure 1:
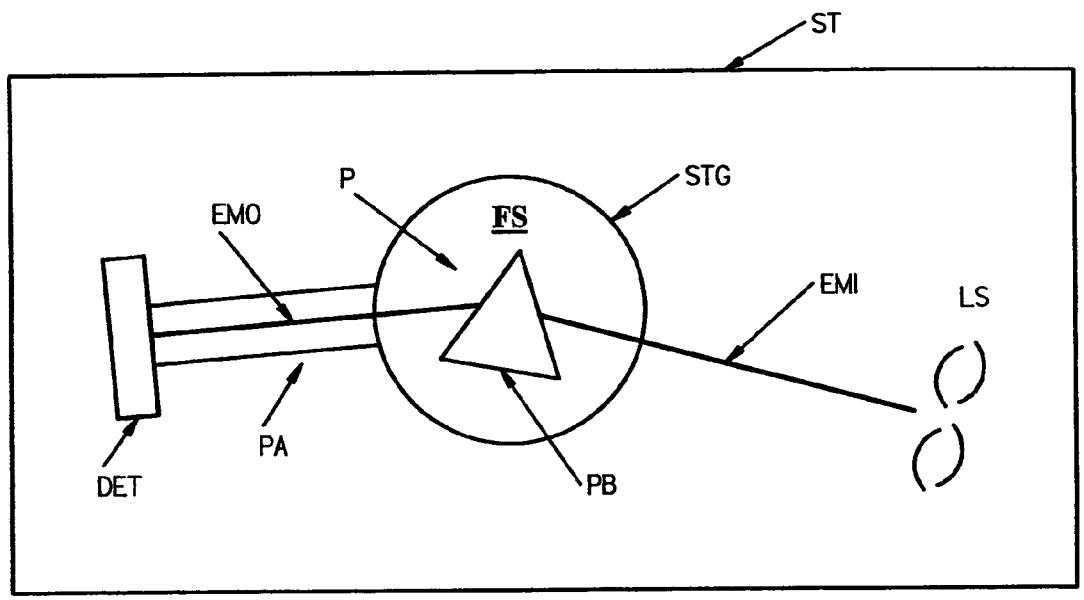
FIGS. 1 and 2 present two possible system configurations for practicing the method of the disclosed invention.
Figure 2:
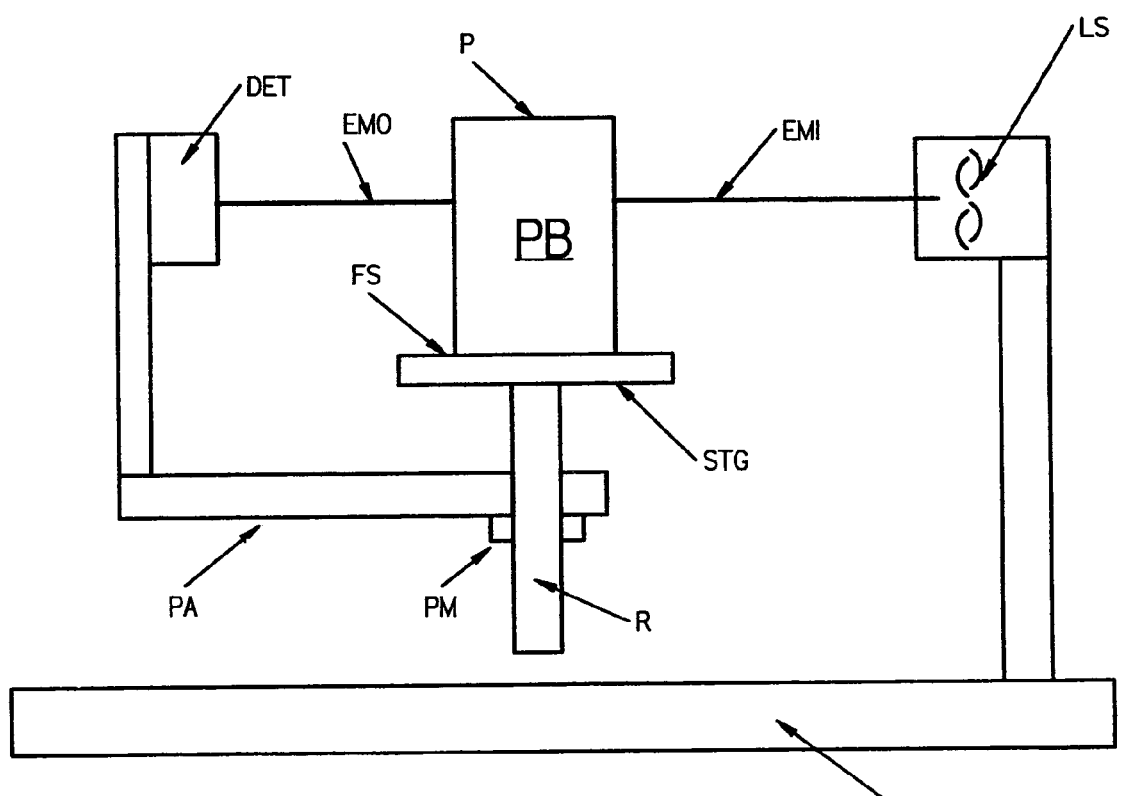

Turning now to the Drawings, there is shown in FIGS. 1 and 2, a System suitable for practicing the disclosed invention. Shown are a structure (ST), a source of electromagnetic radiation (LS), a stage (STG), and a detector (DET). Said stage is shown to have a front side (FS) which is defining of a stage plane, said source of electromagnetic radiation (LS) is fixed in location at an offset from said stage (STG). Said detector (DET) is attached to an arm (PA) which is pivotally secured to said structure (ST) the location of said stage (STG). Note that the relative positioning of said source of electromagnetic radiation (LS), stage (STG) and detector (DET) is such that a beam of electromagnetic radiation (EMI) produced by said source (LS) thereof can be directed to proceed in a plane parallel to, but offset from, the stage plane, and enter said detector (DET) when it is positioned at a detector pivot angle which allows receipt of said beam of electromagnetic radiation, said pivot angle being effected by pivot motion of said arm (PA) which is pivotally secured to said structure the location of said stage (STG). (This can be directly appreciated by considering that the Prism (P) is not present in FIG. 2). Additional sample translation stages can also be present, providing precise prism movement in one or more dimensional space. An adaptor mount can also be present, for the purpose of providing precise mounting of the prism to the stage.

Turning now to FIGS. 3a-3j there are shown various non-limiting designs for Prisms (P) which are suitable for use in the System of FIGS. 1 and 2. It should be appreciated that other prism designs which perform functionally equivalent to the shown prism designs can also be used.

Figure 3A:
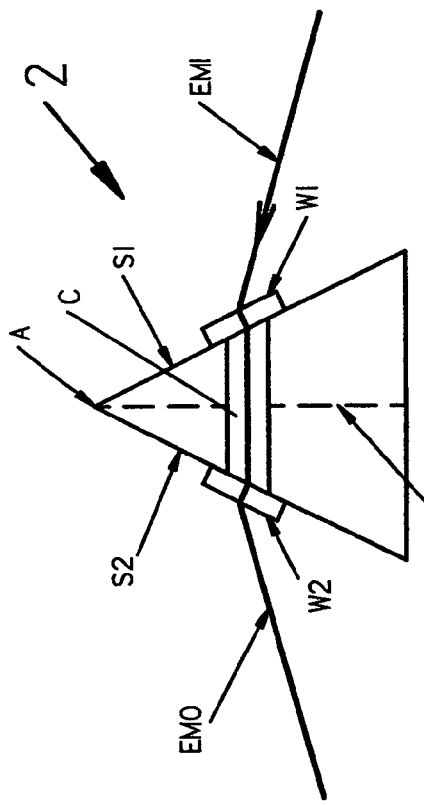
Figure 3B:
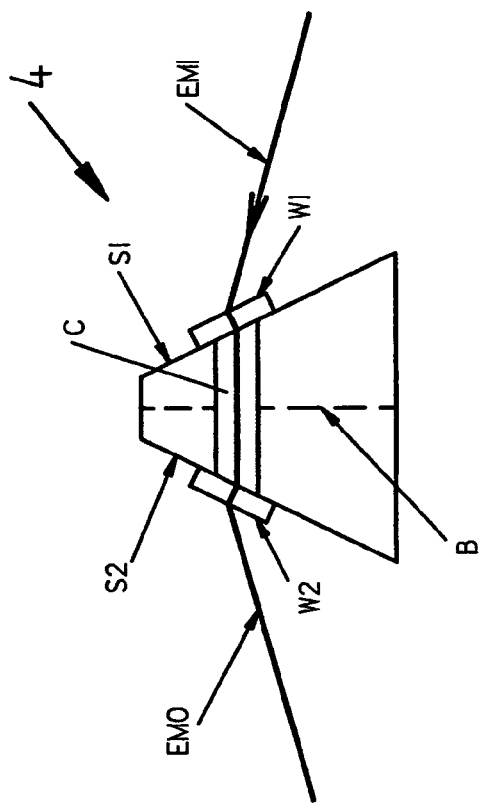
Figure 3C:
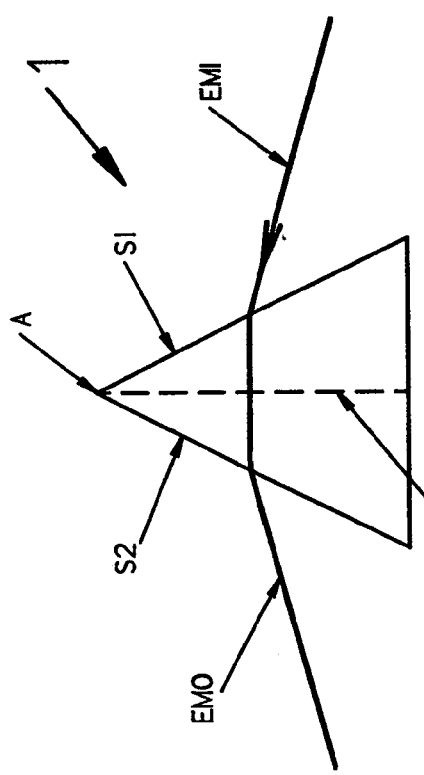
Figure 3D:
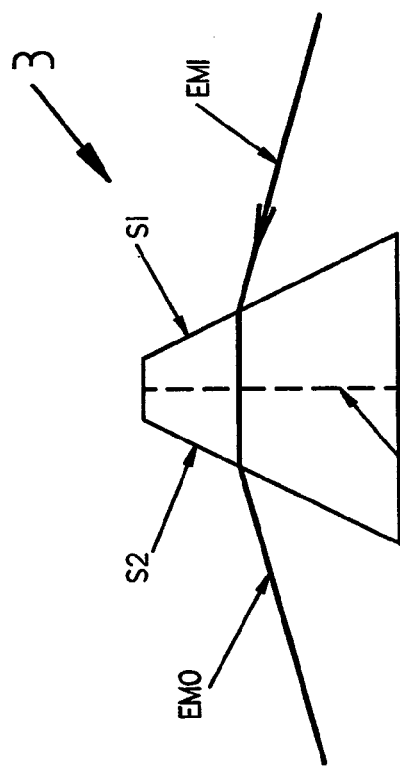

FIG. 3a shows the first (1) system is a triangular prism having a projected apex bisector (B) and first (S1) and second (S2) sides oriented at angles thereto which meet at apex (A); such that in use in a system as shown in FIG. 1 or 2, a beam (EMI) of electromagnetism is caused to enter said triangular shaped prism at the first (S1) side thereof along a locus in a plane parallel to said stage plane and at an angle of incidence to a normal to said first side, pass through said triangular shaped prism, and exit (EMO) the second side of said triangular prism at an exit angle at least partially determined by the refractive index of the material comprising said triangular shaped prism;

FIG. 3b shows a second (2) system is a triangular prism having a projected apex bisector (B) and first (S1) and second (S2) sides oriented at angles thereto which meet at apex (A); there being a cavity (C) within said triangular and means for entering liquid/fluid thereinto, said cavity (C) being bounded internally by a first (W1) and second (W2) windows oriented parallel to said first (S1) and second (S2) sides of said triangular prism respectively; such that in use such in a system as shown in FIG. 1 or 2, liquid/fluid is caused to be present in said cavity (C), and a beam of electromagnetism (EMI) is caused to enter said cavity (C) at the first (S1) side of said triangular prism along a locus in a plane parallel to said stage plane and at an angle of incidence to a normal to said first (S1) side, pass through said first (W1) window, then through said liquid/fluid, then through said second (W2) window and exit as (EMO) at the second side (S2) of said triangular prism at an exit angle at least partially determined by the refractive index of said liquid/fluid;

FIG. 3c shows a third (3) system is a trapazoidal prism having a projected apex bisector (B) and first (S1) and second (S2) sides oriented at angles thereto which projected meet at a virtual apex, (not shown); such that in use in a system as shown in FIG. 1 or 2, a beam (EMI) of electromagnetism is caused to enter said trapezoidal prism at the first (S1) side of said triangular prism along a locus in a plane parallel to said stage plane, pass through said trapazoidal prism, and exit as (EMO) at the second side (S2) of said triangular prism at an exit angle at least partially determined by the refractive index of the material comprising said trapazoidal shaped prism;

FIG. 3d shows a fourth (4) system is a trapazoidal prism having a projected apex bisector (B) and first (S1) and second (S2) sides oriented at angles thereto which meet at a projected virtual apex, (not shown); there being a cavity (C) within said trapazoidal prism and means for entering liquid/fluid thereinto, said cavity (C) being bounded internally by first (S1) and second (S2) windows oriented parallel to said first and second sides of said trapazoidal prism respectively; such that in use in a system as shown in FIG. 1 or 2, that in use liquid/fluid is caused to be present in said cavity (C), and a beam (EMI) of electromagnetism is caused to enter said cavity (C) at the first (S1) side of said trapazoidal prism along a locus in a plane parallel to said stage plane and at an angle of incidence to a normal to said first (S1) side, pass through said first (W1) window, then through said liquid/fluid, then through said second (W2) window and exit the second side of said trapazoidal prism at an exit angle at least partially determined by the refractive index of said liquid/fluid.

FIG. 3e shows a fifth (5) system for use in accurately determining the refractive index of liquid/fluid is a triangular half-prism comprising, as viewed in side elevation, a first (S1) side which meets a second (S2) side oriented at an angle to said first (S1) side, at apex (A); there being a cavity (C) within said triangular half-prism and means for entering liquid/fluid thereinto, said cavity (C) being bounded internally by a first (W1) window oriented parallel to said first (S1) side of said triangular half-prism, a second (W2) window oriented parallel to said second (S2) side of said triangular half-prism and, between said first (S1) and second (S2) sides of said triangular half-prism inside said cavity (C), there being a third (W3) window which is oriented parallel to a mirror image of said second (W2) window taken about said first (S1) side of said triangular half-prism; such that in use in a system as shown in FIG. 1 or 2, liquid is caused to be present in said cavity, and a beam (EMI) of electromagnetism is caused to enter said cavity (C) through said first window (W1) at the first (S1) side of said triangular half-prism along a locus parallel to said stage plane and perpendicular to said first (W1) window, pass sequentially through liquid/fluid, said third (W3) window, liquid/fluid, and then through said second (W2) window and exit the second side of said triangular half-prism at an exit angle at least partially determined by the refractive index of said liquid/fluid.

FIG. 3f shows a sixth (6) system for use in accurately determining the refractive index of liquid/fluid is a triangular half-prism comprising, as viewed in side elevation, a first (S1) side which meets a second (S2) side oriented at an angle to said first (S1) side, at apex (A); there being a cavity (C) within said triangular half-prism and means for entering liquid/fluid thereinto, said cavity (C) being bounded internally by a first (W1) window oriented parallel to said first (S1) side of said triangular half-prism, a second (W2) window oriented parallel to said second (S2) side of said triangular half-prism and; such that in use in a system as shown in FIG. 1 or 2, liquid/fluid is caused to be present in said cavity (C), and a beam (EMI) of electromagnetism is caused to enter said cavity (C) through said first (W1) window at the first (S1) side of said triangular half-prism along a locus parallel to said stage plane and perpendicular to said first (W1) window, pass sequentially through liquid/fluid and then through said second (W2) window and exit (EMO) said triangular half-prism at an exit angle at least partially determined by the refractive index of said liquid/fluid.

FIG. 3g shows a seventh (7) system for use in accurately determining the refractive index of liquid/fluid is a trapazoidal half-prism comprising, as viewed in side elevation, a first (S1) side which meets a second (S2) side oriented at an angle to said first (S1) side, at a projected virtual apex, (not shown); there being a cavity (C) within said trapazoidal half-prism and means for entering liquid/fluid thereinto, said cavity (C) being bounded internally by a first (W1) window oriented parallel to said first (S1) side of said trapazoidal half-prism, a second (W2) window oriented parallel to said second (S2) side of said trapazoidal half-prism and, between said first (S1) and second (S2) sides of said trapazoidal half-prism inside said cavity (C), there being a third (W3) window which is oriented parallel to a mirror image of said second (W2) window taken about said first (S1) side of said trapazoidal half-prism; such that in use in a system as shown in FIG. 1 or 2, liquid/fluid is caused to be present in said cavity (C), and a beam (EMI) of electromagnetism is caused to enter said cavity (C) through said first (W1) window at the first (S1) side of said trapazoidal half-prism along a locus parallel to said stage plane and perpendicular to said first (W1) window, pass sequentially through liquid/fluid, said third (W3) window, liquid/fluid, and then through said second (W2) window and exit (EMO) said trapazoidal half-prism at an exit angle at least partially determined by the refractive index of said liquid/fluid, FIG. 3h shows an eighth (8) system for use in accurately determining the refractive index of liquid/fluid is a trapazoidal half-prism comprising, as viewed in side elevation, a first (S1) side which meets a second (S2) side oriented at an angle to said first (S1) side, at a projected virtual apex (not shown); there being a cavity (C) within said trapazoidal half-prism and means for entering liquid/fluid thereinto, said cavity (C) being bounded internally by a first (W1) window oriented parallel to said first (S1) side of said trapazoidal half-prism, a second (W2) window oriented parallel to said second (S2) side of said trapazoidal half-prism and; such that in use in a system as shown in FIG. 1 or 2, liquid/fluid is caused to be present in said cavity (C), and a beam (EMI) of electromagnetism is caused to enter said cavity (C) through said first (W1) window at the first (S1) side of said trapazoidal half-prism along a locus parallel to said stage plane and perpendicular to said first (W1) window, pass sequentially through liquid/fluid and then through said second (W2) window and exit (EMO) said trapezoidal half-prism at an exit angle at least partially determined by the refractive index of said liquid/fluid.

Note that FIGS. 3g and 3h show an extension (W2E) on the second window (W2), (ie. it projects beyond the extent of the second side (S2)), for use in alignment and accurate determination of the angle at which the first and second sides meet at the apex or virtual apex, (not shown). The extension can be frosted or roughened on one side thereof, or otherwise made non-reflective, such that in use the prism can be positioned on a stage such that an electromagnetic beam (EMI) from the source (LS) thereof reflects directly back from said elongated second window (W2), with the prism then being positioned and rotated and so that said electromagnetic beam from the source thereof reflects directly back from said first (W1) window. The required angle of rotation is the angle at which the first and second sides meet at the apex or virtual apex. The same approach of providing an extended second side (S2) in the FIGS. 3g-3h prisms, can be applied to prisms 3a 3b, 3c, 3d, 3e and 3f. Note that the extension (W2E) of the second window (S2) can be directed out of the page, into the page or away from the apex instead of directed as shown in FIGS. 3g and 3h, extending in any functional direction.

Figure 3I:
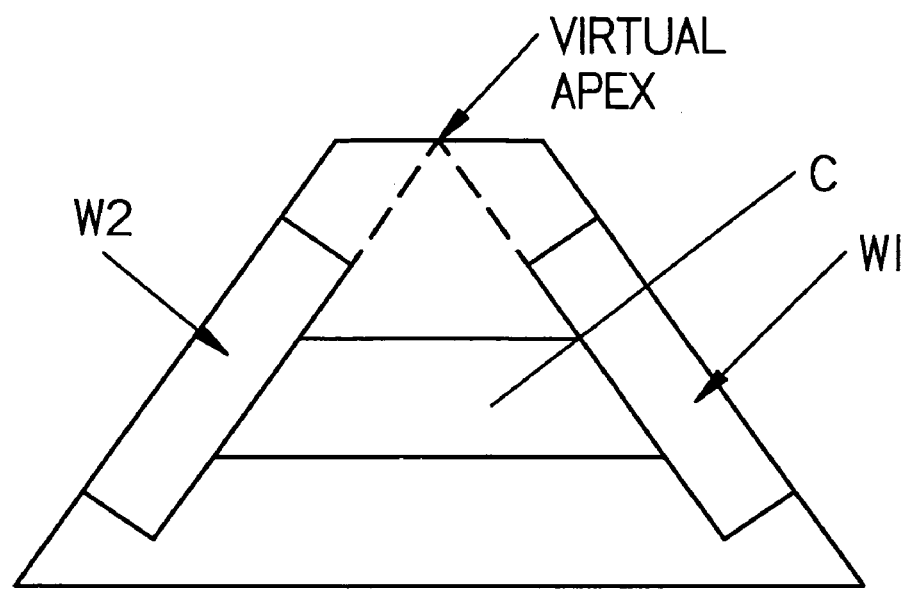
FIGS. 3i and 3j are included to show that windows can be embedded into the sides of prisms.
Figure 3J:
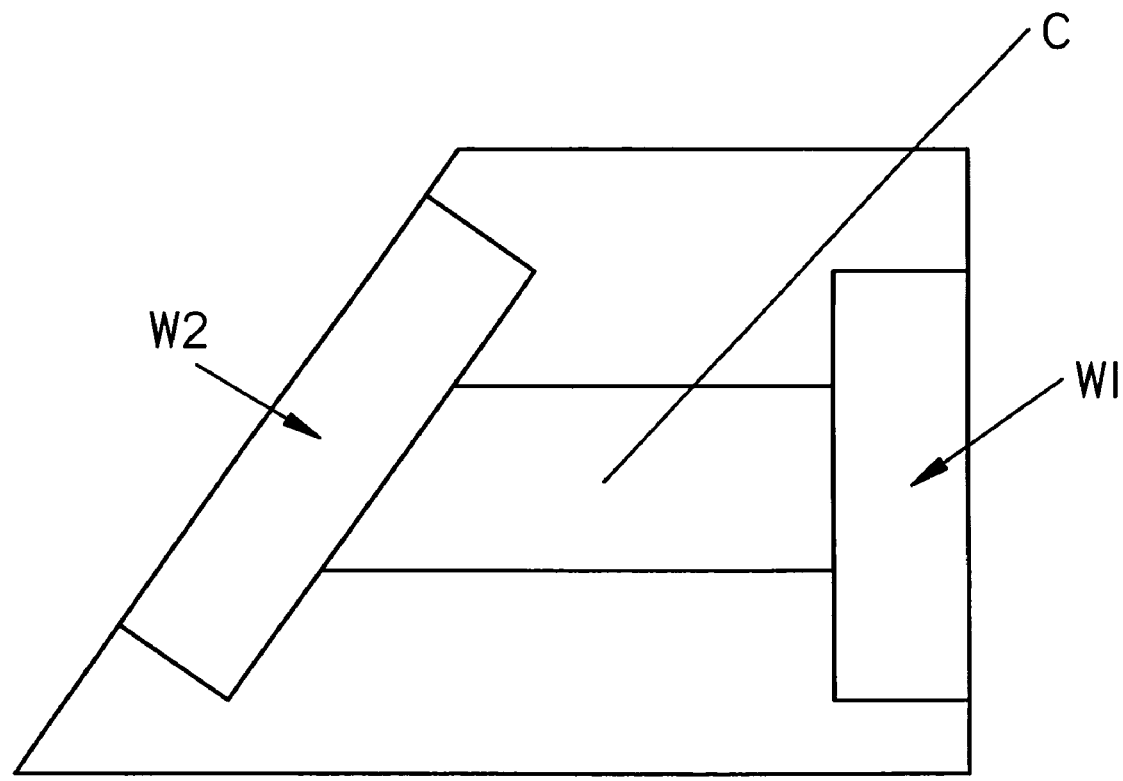

FIGS. 3i and 3j are modified versions of FIGS. 3d and 3h, and are included to show that windows (W1) and (W2) can be embedded into the sides of prisms. Note the Virtual Apex at the intersection of the Projected Inner Surfaces of the First and Second Windows. Said intersection corresponds to the Virtual Apex of the Fluid Trapezoidal Prism when fluid is present in the cavity. This is actually a preferred, although non-limiting approach to embodiment.

Figure 4:
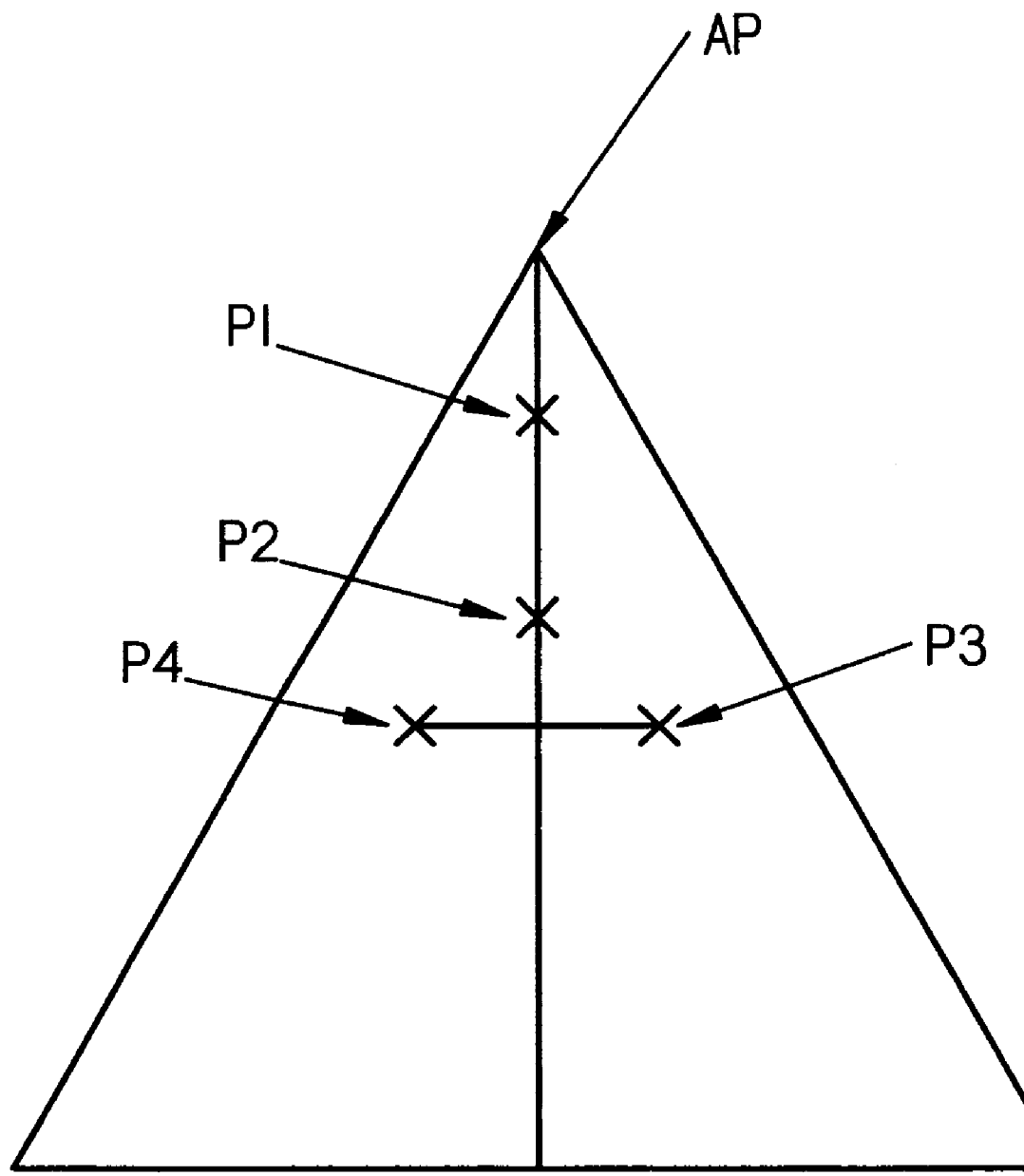
FIG. 4 shows possible, non-limiting, locations of the axis of rotation of a prism during practice of the present invention method.

FIG. 4 shows a Prism with Rotation Axes (P1) (P2) (P3) and (P4) identified. Ideally rotation would be about the Apex (AP), however, where liquid is present in the Prism, this is not practical or even possible. Offset of the rotation axes along the Bisector of the Apex or virtual Apex Angle, and lateral offset of the Rotation Axes from said Bisector of the Apex or Virtual Apex, enters artifacts which require compensation, as described elsewhere in this Specification.

Figure 5A:
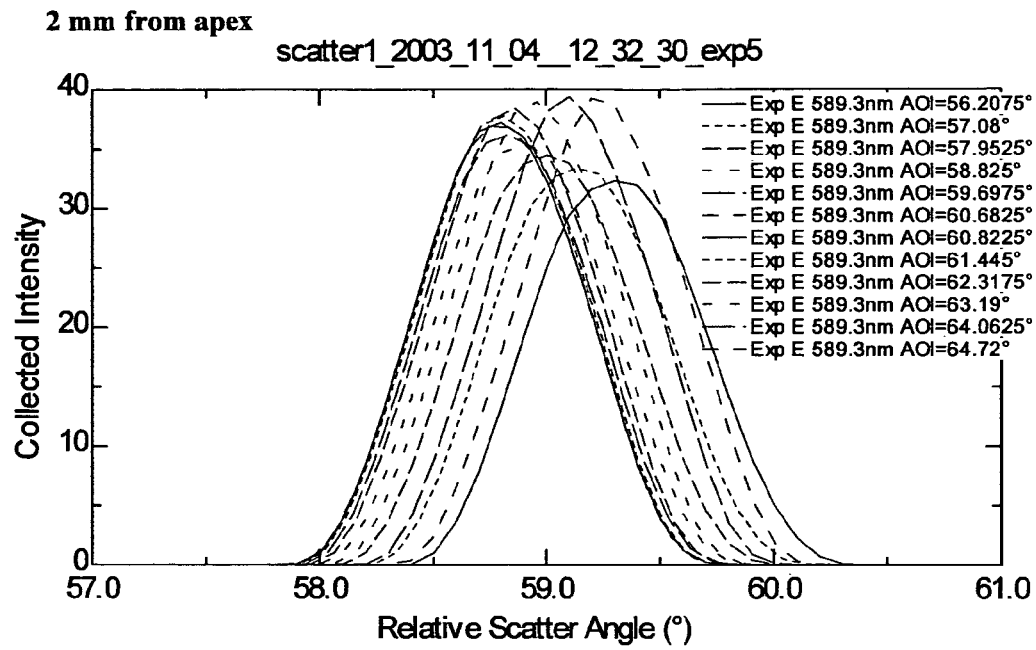
FIGS. 5a and 5b show Intensity vs. Relative Scatter Angle for cases where the Rotation Axes is located in the Prism at 2 (P1) and 10 mm (P2) from an Apex thereof, along the Bisector of the Apex angle.
Figure 5B:
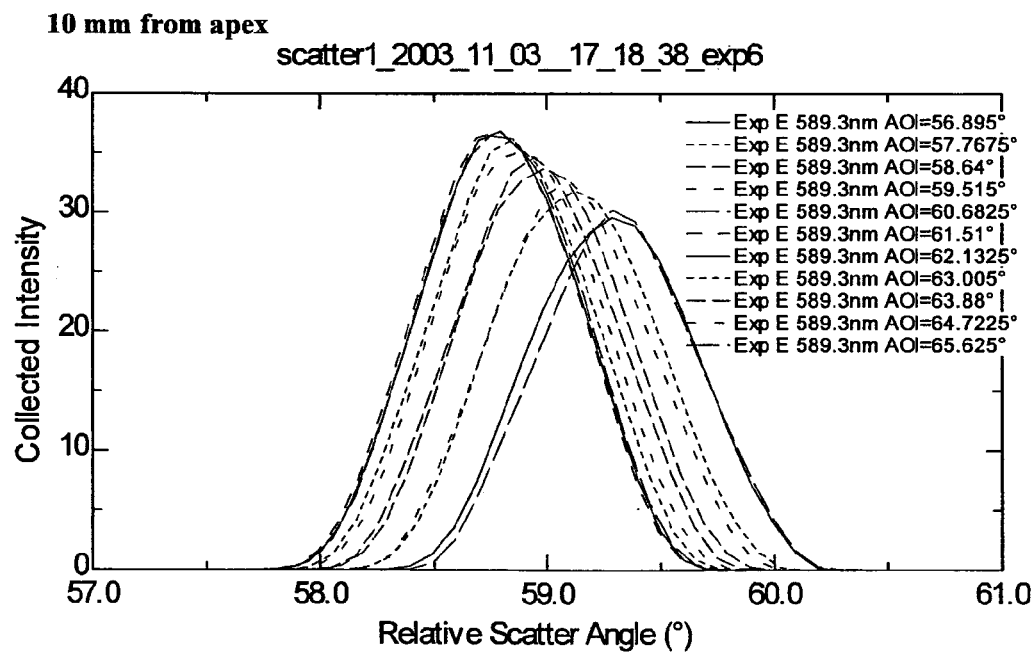
Figure 6A:
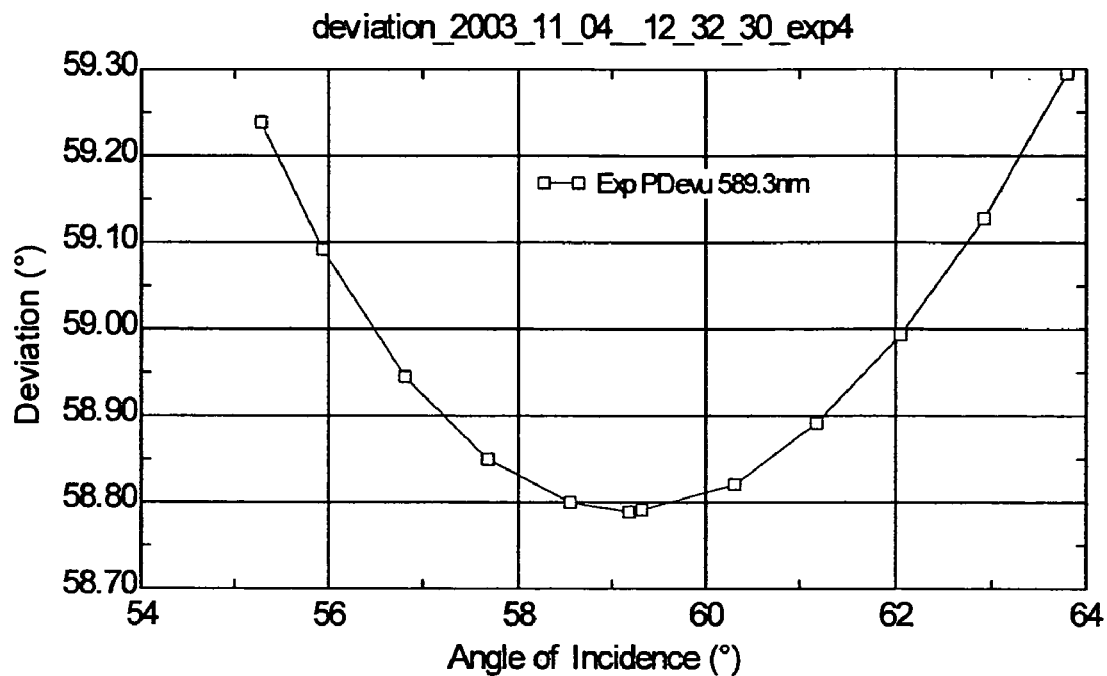
FIGS. 6a and 6b show that when a plot of "Deviation Angle" (as determined from FIGS. 5a and 5b), vs. Angle-of-Incidence of the electromagnetic beam with respect to a normal to the side of the triangular shaped prism onto which it impinges, it is found to demonstrate a Minimum.
Figure 6B:
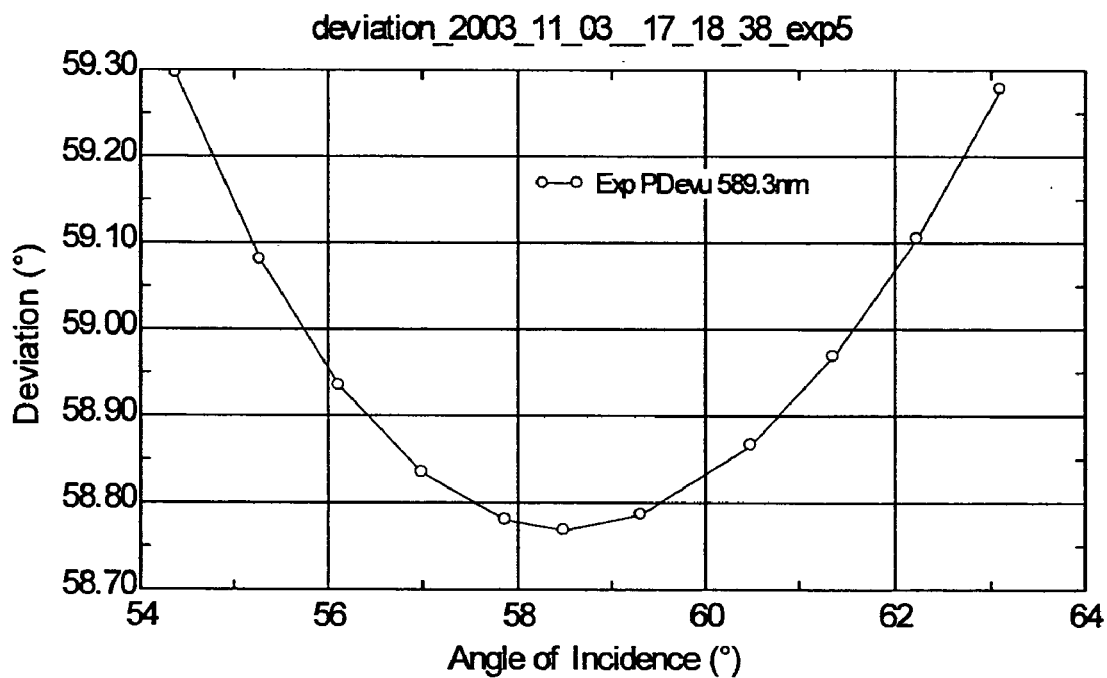
Figure 6C:
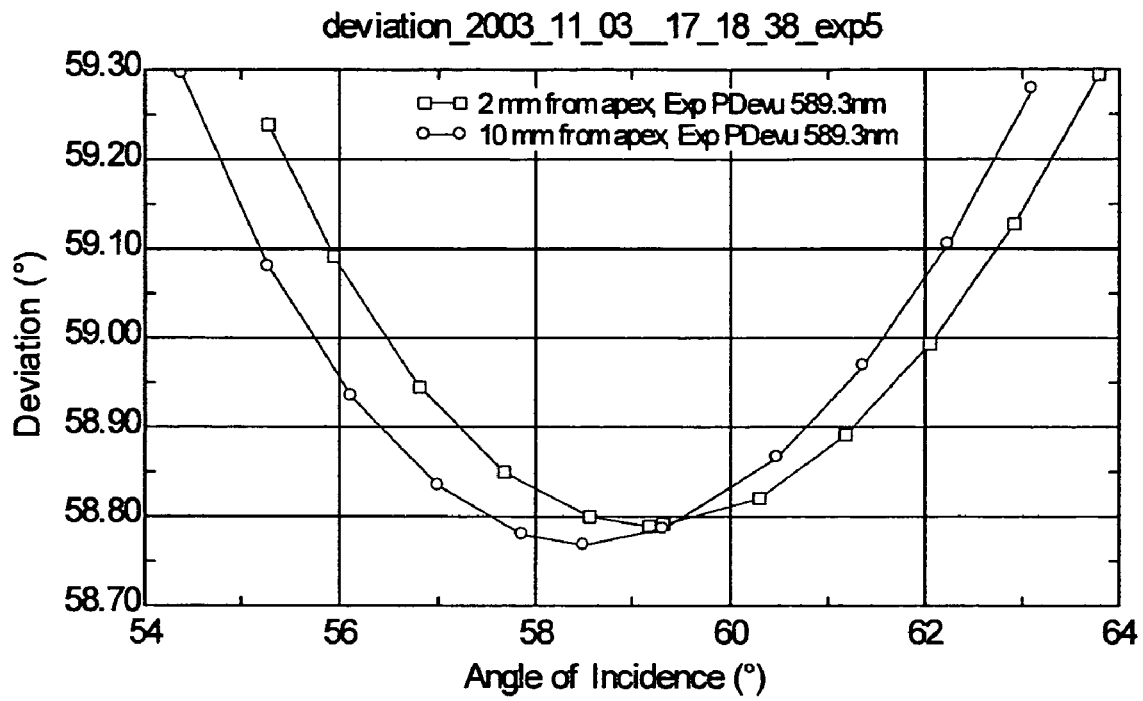
FIG. 6c shows that the plots of FIGS. 6a and 6b intersect.
Figure 6D:
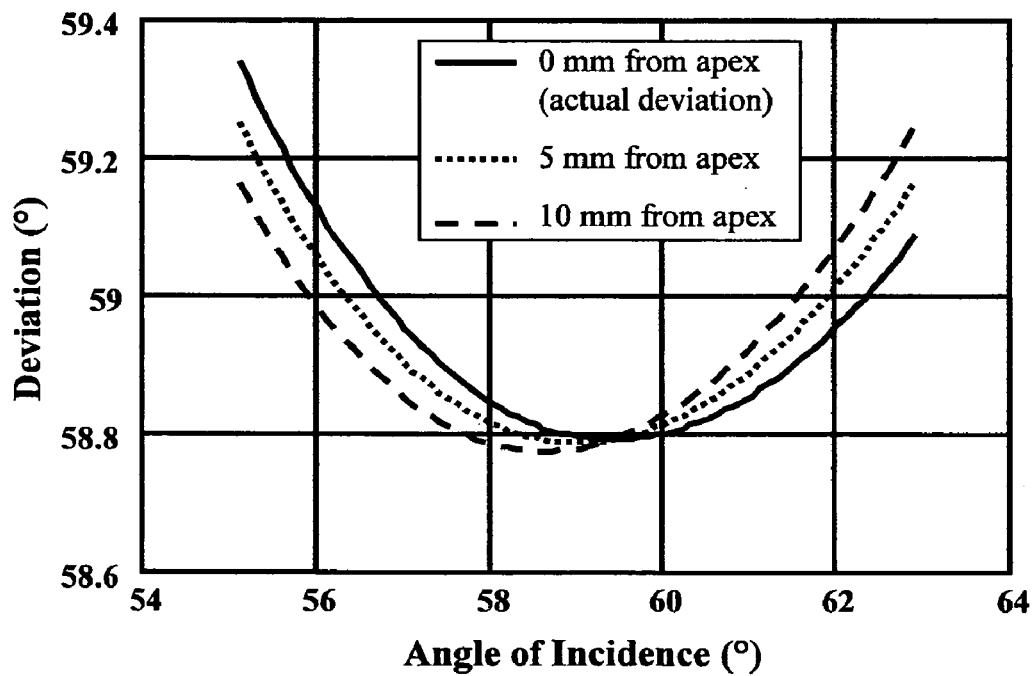
FIG. 6d shows multiple plots corresponding to multiple locations of the axis of rotation along the Bisector of the Apex Angle.

Turning now to FIGS. 5a and 5b, there are shown Intensity vs. Relative Scatter Angle for cases where the Rotation Axes is located in the Prism at 2 mm (P1) and 10 mm (P2) from an Apex or Virtual Apex thereof. As presented in the Disclosure Section, one primary embodiment of the disclosed invention provides that a triangular shaped prism be positioned on a rotatably mounted stage, and that a beam of electromagnetic radiation from a source thereof be caused to impinge upon one side of said triangular shaped prism. FIGS. 5a and 5b show Intensity results for where a Rotatable Stage/Prism combination is caused to be stepped through a sequence of rotation angles, and at each thereof the detector is caused to be rotated about the pivot mounting of the arm to which it is attached, while intensity measurements are taken at a sequence of said detector angular positions. Note that for each position of the rotatable stage, said detected Intensity measurements as a function of detector position, are found to peak. Said peaks are identifying of "Deviation Angle" of the electromagnetic beam caused by its passage through said prism material. (To avoid confusion, please note that the "AOI" notation in FIGS. 5a and 5b is relative to the Stage Normal as is typical Ellipsometric practice, and not to a Normal to a Prism Window). Turning now to FIGS. 6a-6d, it is shown that when a plot of "Deviation Angle" (as determined from FIGS. 5a and 5b), vs. Angle-of-Incidence of the electromagnetic beam with respect to a normal to the side of the triangular shaped prism onto which it impinges, it is found to demonstrate a Minimum. FIGS. 6c and 6d show that an intersection point for a plurality of curves exists.

As disclosed previously, if the electromagnetic beam impinged at the Apex of the triangular shaped prism and said Apex were affixed to the rotatable stage at the location of the horizontally projecting rod, such would be the True Minimum Deviation Angle. However, it is impractical to direct the electromagnetic beam at said Apex, (especially where liquid is to be contained within a cavity in the Triangular shape prism), and as the electromagnetic beam is therefore typically caused to impinge on the triangular shaped prism at a location removed therefrom, said measured/observed Minimum is not a True Minimum Deviation.

Continuing, even if the triangular shaped prism is mounted to the rotatable stage such that a projected locus of the horizontally projected rod to which the rotatable stage is attached, intersects the projected bisector of the Apex angle of the Triangular Shaped Prism, it is found that measured/observed Deviation Angle vs. Angle of Incidence data varies with the distance from said Apex, of the intersection of a projection of the locus of said projecting rod along the projected apex bisector, which defines a center of rotation. FIG. 5c shows that if two sets of data taken with the triangular shaped prism positioned on the rotatable stage such that the projected apex bisector is intersected by the projected locus of the axile means for allowing stage rotation (eg. rod) at two (or more), different distances from the Apex, said sets of data, if plotted on the same graph of Deviation Angle vs. Angle of Incidence, intersect. (It is noted that identification of said intersection point can be determined by fitting mathematical function to the data and mathematically determining their intersection point). Said intersection point is identifying of the Angle-of-Incidence at which the true Minimum Deviation Angle occurs. Importantly, said Minimum Deviation Angle identifying Angle-of-Incidence is the Angle-of-Incidence at which an accurate Refractive Index can be obtained utilizing methodology of the disclosed invention. (See the Detailed description for a better disclosure of the relationship between the Angle-of-Incidence and the Deviation angle). FIG. 6d is included to indicate that if additional similar plots are included, the same Deviation Angle vs. Angle of Incidence, intersection point is achieved.

Figure 7A:
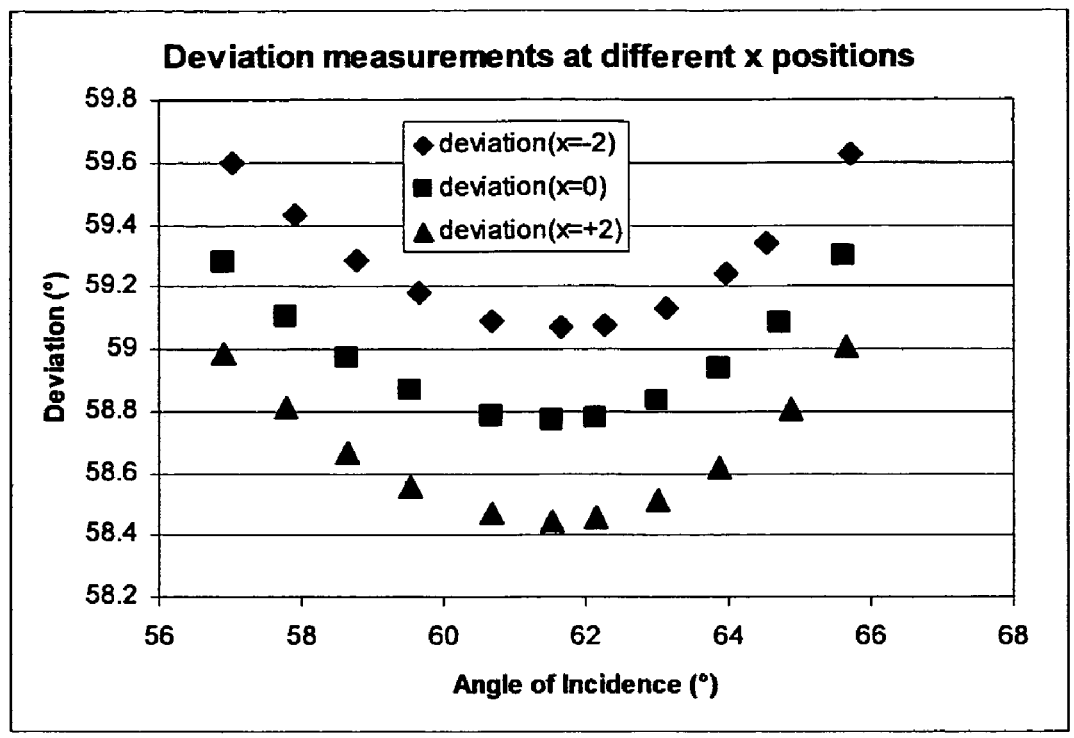
FIG. 7a show the effects of offset of the of the Rotation Axis perpendicular to the locus of the Bisector of the Apex in FIG. 4, (eg. (P3) and (P4)).
Figure 7B:
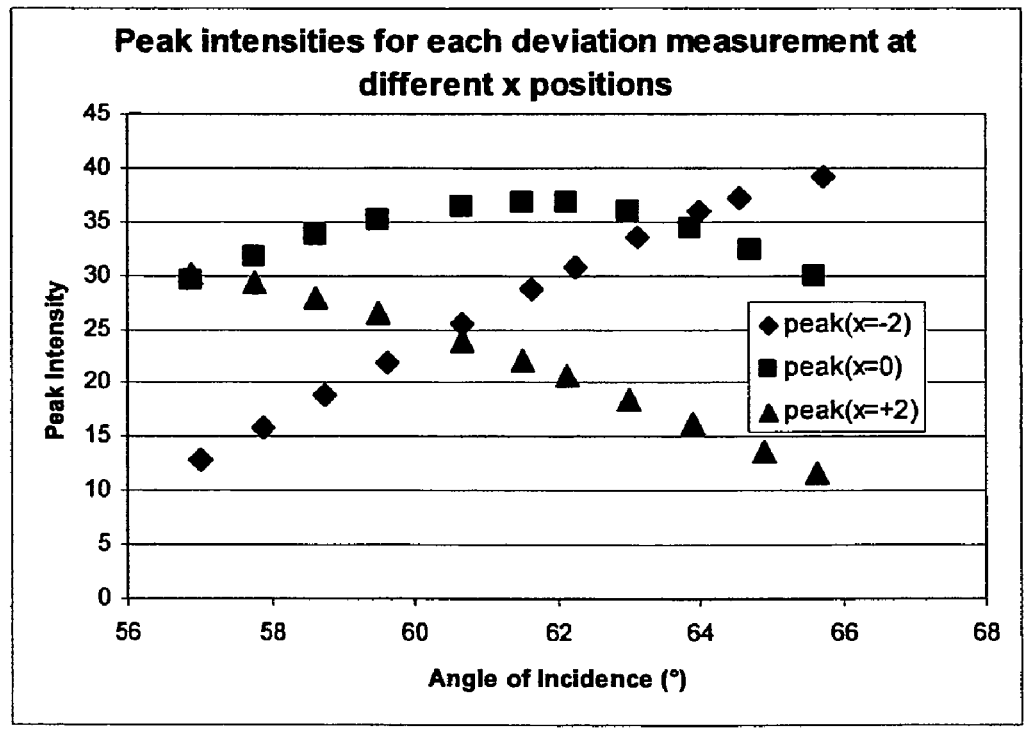
FIG. 7b shows multiple plots of peak electromagnetic radiation peak intensity data vs. Angle of Incidence on the same set of axes. The "lateral" offset position of said prism on said rotatable stage associated with the highest electromagnetic radiation peak intensity near the AOI providing minimum deviation, can be identified. The lateral offset position which provides the minimum slope near the AOI which provides the minimum deviation can also be identified.

FIGS. 7a and 7b show the results of a triangular shaped prism can being positioned on a rotatable stage such that the projected apex bisector of said prism is not intersected by a projected locus of said rod about which the rotatable stage rotates, (eg. see (P3) (P4) in FIG. 4). FIG. 7a shows the effect on Devation Angle, and FIG. 7b shows the effect on Peak Intensities. Said offset can also enter error into accurate determination of Refractive Index of a material. Thus it is necessary to assure that a Triangular Prism is aligned on a rotatable stage such that a projection of the locus of the rod intersects the projected apex bisector, or correct for the offset. As disclosed earlier, this can be accomplished by, for each of a plurality of "lateral" positions of said prism on said rotatable stage, which "lateral" positions are offset from one another along a perpendicular to the projected apex bisector of said prism, obtaining data corresponding to a plurality of rotation positions of said stage about said rod, (ie. axile means for allowing stage rotation), about which the stage rotates. Said data is obtained by causing an electromagnetic beam from said source of electromagnetic radiation to enter the first side prism at an angle of incidence to a normal to the plane of said first side of said prism, and at each angle of incidence, obtaining electromagnetic radiation peak intensity data for each of a plurality of detector position pivot angles, such that the detector position pivot angle at which the peak of the electromagnetic radiation intensity is detected is identified. Assuming said lateral offset of the locus of the projected rod is not too far removed from the projected apex bisector, (it is noted that eye-ball positioning of the prism is sufficient to provide a good result), peak intensity plot data provides information which allows determining any offset. Electromagnetic radiation peak Intensity vs. Angle of Incidence of said electromagnetic radiation beam to a normal to the plane of said first side of said prism can be inspected to demonstrate first and second slopes. If a data plot slope provides a peak at which the slope is zero (0.0), it corresponds to a correct positioning of the prism's projected apex bisector. If slopes are non-zero, the values of said slopes provide information which can be applied to calculate "lateral" positioning of said prism along a locus perpendicular to the projected apex bisector of said prism on said rotatable stage to position said prism such that its projected apex bisector intersects the projected locus of said the rod axile means for allowing stage rotation. It is also possible to simply effectively plot multiple plots of said peak electromagnetic radiation peak intensity data vs. Angle of Incidence on the same set of axes such that the "lateral" offset position of said prism on said rotatable stage associated with the highest electromagnetic radiation peak intensity can be identified. Around the Angle of Incidence whereat the effective minimum deviation angle occurres, said "lateral" position associated with the highest electromagnetic radiation intensity peak is identifying of the location of whereat the projected apex bisector of said prism is intersected by said projected locus of said the axile means for allowing stage rotation. Of course, instead of correcting the system configuration for offsets, the approach of determining what offset exists, and including a correction factor which compensates for it during analysis can be practiced. This can be in the alternative or in combination with the described system correction procedure.

It is again noted that an Alternative approach to compensating lateral offset from said Bisector of the Apex or Virtual Apexisector is to obtain data with a Prism in a first orientation, and then obtain data with the Prism rotated 180 degrees. A "Zone-Averaging" technique can then be applied to the two data sets, corresponding data point pair by corresponding data point pair, which results in a compensation of the lateral offset.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of improving accuracy in determining the refractive index of material or liquid/fluid comprising the steps of:

a) providing a system comprising:
   a structure;
   a source of electromagnetic radiation;
   a rotatable stage; and
   a detector;

said rotatable stage having a front side which is defining of a stage plane, and being rotatably mounted to said structure at an axile means for allowing stage rotation thereabout, about which axile means said rotatable stage can be caused to rotate in said stage plane; said source of electromagnetic radiation being fixed in location at an offset from said rotatable stage, and said detector being attached to an arm which is pivotally secured to said structure the location of said rotatable stage;

the relative positioning of said source of electromagnetic radiation, rotatable stage and detector being such that a beam of electromagnetic radiation produced by said source thereof can be directed to proceed in a plane parallel to, but offset from, the stage plane, and enter said detector when it is positioned at a detector pivot angle which allows receipt of said beam of electromagnetic radiation, said pivot angle being effected by pivot motion of said arm which is pivotally secured to said structure the location of said rotatable stage;

b) placing a prism on the front side of said rotatable stage, said prism being a selection from the group consisting of:

a triangular prism having a projected apex bisector and first and second sides oriented at angles thereto which meet at said apex; such that in use a beam of electromagnetism is caused to enter said triangular shaped prism at the first side thereof along a locus in a plane parallel to said stage plane and at an angle of incidence to a normal to said first side, pass through said triangular shaped prism, and exit the second side of said triangular prism at an exit angle at least partially determined by the refractive index of the material comprising said triangular shaped prism;

a triangular prism having a projected apex bisector and first and second sides oriented at angles thereto which meet at an apex; there being a cavity within said triangular prism and means for entering liquid/fluid thereinto, said cavity being bounded internally by a first and second windows oriented parallel to said first and second sides of said triangular prism respectively; such that in use liquid/fluid is caused to be present in said cavity, and a beam of electromagnetism is caused to enter said cavity at the first side of said triangular prism along a locus in a plane parallel to said stage plane and at an angle of incidence to a normal to said first side, pass through said first window, then through said liquid/fluid, then through said second window and exit the second side of said triangular prism at an exit angle at least partially determined by the refractive index of said liquid/fluid;

a trapezoidal prism having a projected apex bisector and first and second sides oriented at angles thereto which meet at a virtual apex; such that in use a beam of electromagnetism is caused to enter said trapazoidal prism at the first side of said triangular prism along a locus in a plane parallel to said stage plane, pass through said trapazoidal prism, and exit the second side of said triangular prism at an exit angle at least partially determined by the refractive index of the material comprising said trapazoidal shaped prism;

a trapezoidal prism having a projected apex bisector and first and second sides oriented at angles thereto which meet at a virtual apex; there being a cavity within said trapazoidal prism and means for entering liquid/fluid thereinto, said cavity being bounded internally by first and second windows oriented parallel to said first and second sides of said trapazoidal prism respectively; such that in use liquid/fluid is caused to be present in said cavity, and a beam of electromagnetism is caused to enter said cavity at the first side of said trapazoidal prism along a locus in a plane parallel to said stage plane and at an angle of incidence to a normal to said first side, pass through said first window, then through said liquid/fluid, then through said second window and exit the second side of said trapazoidal prism at an exit angle at least partially determined by the refractive index of said liquid/fluid;

said selected prism being positioned on said rotatable stage such that projected apex bisector thereof is intersected by a projected locus of said the axile means for allowing stage rotation, at a first distance removed from said apex or virtual apex;

c) for each of a plurality of rotation positions of said stage about said axile means for allowing stage rotation thereabout, causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles such that the detector position pivot angle at which peak electromagnetic radiation intensity is detected is identified;

d) providing an effective plot of deviation angles determined from said detector position pivot angles at which peak electromagnetic radiation intensity is present, vs. the angle of incidence of said beam of electromagnetic radiation to the normal to said first side of said prism, which effective plot demonstrates a minimum;

e) moving the selected prism on said stage such that it becomes positioned on said rotatable stage such that projected apex bisector thereof is intersected by a projected locus of said the axile means for allowing stage rotation, at a second distance removed from said apex or virtual apex, and repeating steps c and d;

f) locating intersection of the effective plots determined in the first and second practice of step d, and the minimum deviation angle identifying angle of incidence of the electromagnetic beam with respect to a normal to the plane of said first side of said prism, at said intersection;

g) utilizing data obtained at the angle of incidence and corresponding minimum deviation angle identified in step f in calculations to determine an accurate index of refraction for the material or liquid/fluid, or utilizing data obtained at other than said angle of incidence identified in step f and utilizing data obtained in steps b-f to derive a correction to data obtained at other than said angle of incidence; and h) tangibly displaying at least one selection from the group consisting of:
at least some electromagnetic radiation intensity data obtained in step c;
at least one effective plot provided in practice of step d or step f; and
the accurate index of refraction determined in step g.

2. A method of improving accuracy in determining the refractive index of material or liquid/fluid as in claim 1, which further comprises assuring that said selected prism is positioned on said rotatable stage such that projected apex bisector of said prism is intersected a projected locus of said the axile means for allowing stage rotation, at one or more distances removed from said apex or virtual apex in steps a and e, said steps comprising a sequence of steps selected from A and B:

a1) for each of at least two "lateral" positions of said prism on said rotatable stage, which "lateral" positions are offset from one another along a perpendicular to the projected apex bisector of said prism, obtaining data corresponding to a plurality of rotation positions of said stage about said axile means for allowing stage rotation thereabout, said data being obtained by causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles;

a2) identifying first and second slopes of effective plots of electromagnetic radiation peak intensity vs. angle of incidence of said electromagnetic radiation beam to a normal to the plane of said first side of said prism corresponding to said two lateral positions of said prism on said rotatable stage;

a3) applying said first and second slopes determined in step a2) to calculate "lateral" positioning of said prism along a locus perpendicular to the projected apex bisector of said prism on said rotatable stage to direct the positioning said prism such that its projected apex bisector intersects the a projected locus of said the axile means for allowing stage rotation, or to derive a correction factor for application to data obtained with the prism positioned other than with the prism projected apex bisector being intersected a projected locus of said the axile means for allowing stage rotation.

b1) for one "lateral" position of said prism on said rotatable stage, which "lateral" position is along a perpendicular to the projected apex bisector of said prism, obtaining data corresponding to a plurality of rotation positions of said stage about said axile means for allowing stage rotation thereabout, said data being obtained by causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles;

b2) identifying a slope of effective plot of electromagnetic radiation peak intensity vs. angle of incidence of said electromagnetic radiation beam to a normal to the plane of said first side of said prism corresponding to said lateral position of said prism on said rotatable stage;

b3) applying said slope determined in step b2) to calculate "lateral" positioning of said prism along a locus perpendicular to the projected apex bisector of said prism on said rotatable stage to direct the positioning said prism such that its projected apex bisector intersects the a projected locus of said the axile means for allowing stage rotation, or to derive a correction factor for application to data obtained with the prism positioned other than with the prism projected apex bisector being intersected a projected locus of said the axile means for allowing stage rotation.

3. A method of improving accuracy in determining the refractive index of material or liquid/fluid as in claim 2, which further comprises assuring that said selected prism is positioned on said rotatable stage such that projected apex bisector of said prism is intersected a projected locus of said the axile means for allowing stage rotation, at one or more distances removed from said apex or virtual apex in steps a and e, said steps comprising:

a1) for each of a plurality of "lateral" positions of said prism on said rotatable stage, which "lateral" positions are offset from one another along a perpendicular to the projected apex bisector of said prism, obtaining data corresponding to a plurality of rotation positions of said stage about said axile means for allowing stage rotation thereabout, said data being obtained by causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles such that the detector position pivot angle at which peak electromagnetic radiation intensity is detected is identified;

a2) effectively plotting at least some of said plots of said peak electromagnetic radiation peak intensity data vs. angle of incidence obtained in step a1, on the same set of axes such that the "lateral" offset position of said prism on said rotatable stage associated with the highest electromagnetic radiation peak intensity around the angle of incidence where the effective minimum deviation occurs can be identified, said "lateral" position associated with the highest electromagnetic radiation peak intensity being identifying of the location of whereat the projected apex bisector of said prism is intersected by said projected locus of said the axile means for allowing stage rotation, and applying said information to direct positioning of said prism on said stage rotatable stage so that the prism projected apex bisector intersects a projected locus of said the axile means for allowing stage rotation, or to derive a correction factor for application to data obtained with the prism positioned other than with the prism projected apex bisector being intersected a projected locus of said the axile means for allowing stage rotation.

4. A method of improving accuracy in determining the refractive index of material or liquid/fluid as in claim 1, which further comprises assuring that said selected prism is positioned on said rotatable stage such that projected apex bisector of said prism is intersected a projected locus of said the axile means for allowing stage rotation, at one or more distances removed from said apex or virtual apex in steps a and e, said steps comprising:

a1) for each of a plurality of "lateral" positions of said prism on said rotatable stage, which "lateral" positions are offset from one another along a perpendicular to the projected apex bisector of said prism, obtaining data corresponding to a plurality of rotation positions of said stage about said axile means for allowing stage rotation thereabout, said data being obtained by causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles such that the detector position pivot angle at which peak electromagnetic radiation intensity is detected is identified;

a2) effectively plotting at least some of said plots of said peak electromagnetic radiation peak intensity data vs. angle of incidence obtained in step a1, on the same set of axes such that the "lateral" offset position of said prism on said rotatable stage associated with the highest electromagnetic radiation peak intensity around the angle of incidence where the effective minimum deviation occurs can be identified, said "lateral" position associated with the highest electromagnetic radiation peak intensity being identifying of the location of whereat the projected apex bisector of said prism is intersected by said projected locus of said the axile means for allowing stage rotation, and applying said information to direct positioning of said prism on said stage rotatable stage so that the prism projected apex bisector intersects a projected locus of said the axile means for allowing stage rotation, or to derive a correction factor for application to data obtained with the prism positioned other than with the prism projected apex bisector being intersected a projected locus of said the axile means for allowing stage rotation.

5. A method of improving accuracy in determining the refractive index of material or liquid/fluid as in claim 4 which further comprises a sequence of steps selected from A and B:

a3) identifying first and second slopes of two electromagnetic radiation peak intensity vs. angle of incidence of said electromagnetic radiation beam to a normal to the plane of said first side of said prism, corresponding to two lateral positions of said prism on said rotatable stage;

a4) in addition to use of determination of the highest intensity of the electromagnetic radiation determined in step a1, applying said first and second slopes determined in step a3) to calculate "lateral" positioning of said prism along a locus perpendicular to the projected apex bisector of said prism on said rotatable stage to direct positioning said prism such that its projected apex bisector intersects the a projected locus of said the axile means for allowing stage rotation, or to derive a correction factor for application to data obtained with the prism positioned other than with the prism projected apex bisector is being intersected a projected locus of said the axile means for allowing stage rotation;

b3) identifying one slope of two electromagnetic radiation peak intensity vs. angle of incidence of said electromagnetic radiation beam to a normal to the plane of said first side of said prism, corresponding to one lateral position of said prism on said rotatable stage;

b4) in addition to use of determination of the highest intensity of the electromagnetic radiation determined in step a1, applying said slope determined in step b3) to calculate "lateral" positioning of said prism along a locus perpendicular to the projected apex bisector of said prism on said rotatable stage to direct positioning said prism such that its projected apex bisector intersects the a projected locus of said the axile means for allowing stage rotation, or to derive a correction factor for application to data obtained with the prism positioned other than with the prism projected apex bisector is being intersected a projected locus of said the axile means for allowing stage rotation.

6. A method of improving accuracy in determining the refractive index of material or liquid/fluid comprising the steps of:

a) providing a system comprising:
a structure;
a source of electromagnetic radiation;
a stage; and
a detector;

said stage having a front side which is defining of a stage plane, and being rotatably mounted to said structure at an axile means for allowing stage rotation thereabout, about which axile means said stage can be caused to rotate in said stage plane; said source of electromagnetic radiation being fixed in location at an offset from said stage, and said detector being attached to an arm which is pivotally secured to said structure the location of said stage;

the relative positioning of said source of electromagnetic radiation, stage and detector being such that a beam of electromagnetic radiation produced by said source thereof can be directed to proceed in a plane parallel to, but offset from, the stage plane, and enter said detector when it is positioned at a detector pivot angle which allows receipt of said beam of electromagnetic radiation, said pivot angle being effected by pivot motion of said arm which is pivotally secured to said structure the location of said stage;

b) placing a prism on the front side of said stage, said prism being a selection from the group consisting of:
a trapazoidal half-prism comprising, as viewed in side elevation, a first side which meets a second side oriented at an angle to said first side, at a virtual apex; there being a cavity within said trapazoidal half-prism and means for entering liquid/fluid thereinto, said cavity being bounded internally by a first window oriented parallel to said first side of said trapazoidal half-prism, a second window oriented parallel to said second side of said trapazoidal half-prism and, between said first and second sides of said trapazoidal half-prism inside said cavity, there being a third window which is oriented parallel to a mirror image of said second window taken about said first side of said trapazoidal half-prism; such that in use liquid/fluid is caused to be present in said cavity, and a beam of electromagnetism is caused to enter said cavity through said first window at the first side of said trapazoidal half-prism along a locus parallel to said stage plane and perpendicular to said first window, pass sequentially through liquid/fluid, said third window, liquid/fluid, and then through said second window and exit the second side of said trapazoidal half-prism at an exit angle at least partially determined by the refractive index of said liquid/fluid;

a triangular half-prism comprising, as viewed in side elevation, a first side which meets a second side oriented at an angle to said first side, at an apex; there being a cavity within said triangular half-prism and means for entering liquid/fluid thereinto, said cavity being bounded internally by a first window oriented parallel to said first side of said triangular half-prism, a second window oriented parallel to said second side of said triangular half-prism and, between said first and second sides of said triangular half-prism inside said cavity, there being a third window which is oriented parallel to a mirror image of said second window taken about said first side of said triangular half-prism; such that in use liquid/fluid is caused to be present in said cavity, and a beam of electromagnetism is caused to enter said cavity through said first window at the first side of said triangular half-prism along a locus parallel to said stage plane and perpendicular to said first window, pass sequentially through liquid/fluid, said third window, liquid/fluid, and then through said second window and exit the second side of said triangular half-prism at an exit angle at least partially determined by the refractive index of said liquid/fluid;

a triangular half-prism comprising, as viewed in side elevation, a first side which meets a second side oriented at an angle to said first side, at an apex; there being a cavity within said triangular half-prism and means for entering liquid/fluid thereinto, said cavity being bounded internally by a first window oriented parallel to said first side of said triangular half-prism, a second window oriented parallel to said second side of said triangular half-prism and; such that in use liquid/fluid is caused to be present in said cavity, and a beam of electromagnetism is caused to enter said cavity through said first window at the first side of said triangular half-prism along a locus parallel to said stage plane and perpendicular to said first window, pass sequentially through liquid/fluid and then through said second window and exit the second side of said triangular half-prism at an exit angle at least partially determined by the refractive index of said liquid/fluid;

a trapazoidal half-prism comprising, as viewed in side elevation, a first side which meets a second side oriented at an angle to said first side, at a virtual apex; there being a cavity within said trapazoidal half-prism and means for entering liquid/fluid thereinto, said cavity being bounded internally by a first window oriented parallel to said first side of said trapazoidal half-prism, a second window oriented parallel to said second side of said trapazoidal half-prism and; such that in use liquid/fluid is caused to be present in said cavity, and a beam of electromagnetism is caused to enter said cavity through said first window at the first side of said trapazoidal half-prism along a locus parallel to said stage plane and perpendicular to said first window, pass sequentially through liquid/fluid and then through said second window and exit the second side of said trapazoidal half-prism at an exit angle at least partially determined by the refractive index of said liquid/fluid;

c) causing an electromagnetic beam from said source of electromagnetic radiation to enter the first window of said prism at a angle of incidence to a normal, inclusive of the normal, to the plane of said first side of said prism, and obtaining electromagnetic radiation intensity data for each of a plurality of detector position pivot angles such that the detector position pivot angle at which peak electromagnetic radiation intensity is detected is identified;

d) utilizing data obtained in calculations to determine an accurate index of refraction for the liquid/fluid; and tangibly displaying said accurate index of refraction value determined in step d.

7. A method of improving accuracy in determining the refractive index of material or liquid/fluid as in claim 6, which further comprises:

a1) causing an electromagnetic beam from said source of electromagnetic radiation to enter the first window of said prism at a angle of incidence to a normal to the plane of said first side of said prism but offset from the locus of the electromagnetic beam in step c, and obtaining electromagnetic radiation intensity data for each of a plurality of detector position pivot angles such that the detector position pivot angle at which peak electromagnetic radiation intensity is detected is identified;

a2) utilizing data obtained in step a1 and step c in claim 6 to determine the absorption or extinction coefficient of the liquid/fluid.

8. A method of determining absorption or extinction coefficient of a material or liquid/fluid comprising the steps of:

a) providing a system comprised of:
a structure;
a source of electromagnetic radiation;
a stage;
a detector;

and providing and placing on said stage, a prism selected from the group consisting of:

a triangular prism having a projected apex bisector and first and second sides oriented at angles thereto which meet at an apex; such that in use a beam of electromagnetism is caused to enter said triangular shaped prism at the first side thereof along a locus in a plane parallel to said stage plane and at an angle of incidence to a normal to said first side, pass through said triangular shaped prism, and exit the second side of said triangular prism at an exit angle at least partially determined by the refractive index of the material comprising said triangular shaped prism;

a triangular prism having a projected apex bisector and first and second sides oriented at angles thereto which meet at an apex; there being a cavity within said triangular and means for entering liquid/fluid thereinto, said cavity being bounded internally by a first and second windows oriented parallel to said first and second sides of said triangular prism respectively; such that in use liquid/fluid is caused to be present in said cavity, and a beam of electromagnetism is caused to enter said cavity at the first side of said triangular prism along a locus in a plane parallel to said stage plane and at an angle of incidence to a normal to said first side, pass through said first window, then through said liquid/fluid, then through said second window and exit the second side of said triangular prism at an exit angle at least partially determined by the refractive index of said liquid/fluid;

a trapazoidal prism having a projected apex bisector and first and second sides oriented at angles thereto which meet at a virtual apex; such that in use a beam of electromagnetism is caused to enter said trapazoidal prism at the first side of said triangular prism along a locus in a plane parallel to said stage plane, pass through said trapazoidal prism, and exit the second side of said triangular prism at an exit angle at least partially determined by the refractive index of the material comprising said trapezoidal shaped prism;

a trapezoidal prism having a projected apex bisector and first and second sides oriented at angles thereto which meet at a virtual apex; there being a cavity within said trapazoidal prism and means for entering liquid/fluid thereinto, said cavity being bounded internally by first and second windows oriented parallel to said first and second sides of said trapazoidal prism respectively; such that in use liquid/fluid is caused to be present in said cavity, and a beam of electromagnetism is caused to enter said cavity at the first side of said trapazoidal prism along a locus in a plane parallel to said stage plane and at an angle of incidence to a normal to said first side, pass through said first window, then through said liquid/fluid, then through said second window and exit the second side of said trapazoidal prism at an exit angle at least partially determined by the refractive index of said liquid/fluid;

a triangular half-prism comprising, as viewed in side elevation, a first side which meets a second side oriented at an angle to said first side, at an apex; there being a cavity within said triangular half-prism and means for entering liquid/fluid thereinto, said cavity being bounded internally by a first window oriented parallel to said first side of said triangular half-prism, a second window oriented parallel to said second side of said triangular half-prism and, between said first and second sides of said triangular half-prism inside said cavity, there being a third window which is oriented parallel to a mirror image of said second window taken about said first side of said triangular half-prism; such that in use liquid/fluid is caused to be present in said cavity, and a beam of electromagnetism is caused to enter said cavity through said first window at the first side of said triangular half-prism along a locus parallel to said stage plane and perpendicular to said first window, pass sequentially through liquid/fluid, said third window, liquid/fluid, and then through said second window and exit the second side of said triangular half-prism at an exit angle at least partially determined by the refractive index of said liquid/fluid; and a triangular half-prism comprising, as viewed in side elevation, a first side which meets a second side oriented at an angle to said first side, at an apex; there being a cavity within said triangular half-prism and means for entering liquid/fluid thereinto, said cavity being bounded internally by a first window oriented parallel to said first side of said triangular half-prism, a second window oriented parallel to said second side of said triangular half-prism and; such that in use liquid/fluid is caused to be present in said cavity, and a beam of electromagnetism is caused to enter said cavity through said first window at the first side of said triangular half-prism along a locus parallel to said stage plane and perpendicular to said first window, pass sequentially through liquid/fluid and then through said second window and exit the second side of said triangular half-prism at an exit angle at least partially determined by the refractive index of said liquid/fluid;

a trapazoidal half-prism comprising, as viewed in side elevation, a first side which meets a second side oriented at an angle to said first side, at a virtual apex; there being a cavity within said trapazoidal half-prism and means for entering liquid/fluid thereinto, said cavity being bounded internally by a first window oriented parallel to said first side of said trapazoidal half-prism, a second window oriented parallel to said second side of said trapazoidal half-prism and, between said first and second sides of said trapazoidal half-prism inside said cavity, there being a third window which is oriented parallel to a mirror image of said second window taken about said first side of said trapazoidal half-prism; such that in use liquid/fluid is caused to be present in said cavity, and a beam of electromagnetism is caused to enter said cavity through said first window at the first side of said trapazoidal half-prism along a locus parallel to said stage plane and perpendicular to said first window, pass sequentially through liquid/fluid, said third window, liquid/fluid, and then through said second window and exit the second side of said trapazoidal half-prism at an exit angle at least partially determined by the refractive index of said liquid/fluid;

a trapazoidal half-prism comprising, as viewed in side elevation, a first side which meets a second side oriented at an angle to said first side, at a virtual apex; there being a cavity within said trapazoidal half-prism and means for entering liquid/fluid thereinto, said cavity being bounded internally by a first window oriented parallel to said first side of said trapazoidal half-prism, a second window oriented parallel to said second side of said trapazoidal half-prism and; such that in use liquid/fluid is caused to be present in said cavity, and a beam of electromagnetism is caused to enter said cavity through said first window at the first side of said trapazoidal half-prism along a locus parallel to said stage plane and perpendicular to said first window, pass sequentially through liquid/fluid and then through said second window and exit the second side of said triangular half-prism at an exit angle at least partially determined by the refractive index of said liquid/fluid;

b) sequentially causing a beam of electromagnetic radiation from said source thereof to pass through said prism at least two different distances from said apex or virtual apex such that the path lengths through said prism are different, and measuring the respective intensities of electromagnetic radiation exiting said prism;

c) forming at least one ratio of two so measured electromagnetic radiation intensities, noting its deviation from 1.0, and from said deviation determining the absorbence or extinction coefficient of said material or liquid/fluid, in view of known, different, path lengths in said material or liquid/fluid through which said electromagnetic radiation passes; and tangibly displaying the absorption or extinction coefficient value of said material or liquid/fluid determined in practice of step c.

9. A method as in claim 8 in which a triangular or trapezoidal prism is selected and in which the electromagnetic beam is caused to enter thereinto at an angle-of-incidence which is substantially the minimum deviation angle;

said method further comprising the step of determining said minimum deviation angle by, for a plurality of electromagnetic beam angles of incidence entry to said triangular or trapazoidal prism, determining a minimum in an effective plot of deviation angles determined from detector position pivot angles at which peak electromagnetic radiation intensity is present, vs. the angle of incidence of said beam of electromagnetic radiation to the normal to said first side of said prism.

10. A method of aligning a system for application in accurately determining the refractive index of material or liquid/fluid which comprises:
  a) providing said system which comprises:
    a structure;
    a source of electromagnetic radiation;
    a rotatable stage; and
    a detector;
  said rotatable stage having a front side which is defining of a stage plane, and being rotatably mounted to said structure at an axile means for allowing stage rotation thereabout, about which axile means said rotatable stage can be caused to rotate in said stage plane; said source of electromagnetic radiation being fixed in location at an offset from said rotatable stage, and said detector being attached to an arm which is pivotally secured to said structure the location of said rotatable stage;
  the relative positioning of said source of electromagnetic radiation, rotatable stage and detector being such that a beam of electromagnetic radiation produced by said source thereof can be directed to proceed in a plane parallel to, but offset from, the stage plane, and enter said detector when it is positioned at a detector pivot angle which allows receipt of said beam of electromagnetic radiation, said pivot angle being effected by pivot motion of said arm which is pivotally secured to said structure the location of said rotatable stage;
  b) placing a prism on the front side of said rotatable stage, said prism being a selection from the group consisting of:
    a triangular prism having a projected apex bisector and first and second sides oriented at angles thereto which meet at an apex; such that in use a beam of electromagnetism is caused to enter said triangular shaped prism at the first side thereof along a locus in a plane parallel to said stage plane and at an angle of incidence to a normal to said first side, pass through said triangular shaped prism, and exit the second side of said triangular prism at an exit angle at least partially determined by the refractive index of the material comprising said triangular shaped prism;
    a triangular prism having a projected apex bisector and first and second sides oriented at angles thereto which meet at an apex; there being a cavity within said triangular and means for entering liquid/fluid thereinto, said cavity being bounded internally by a first and second windows oriented parallel to said first and second sides of said triangular prism respectively; such that in use liquid/fluid is caused to be present in said cavity, and a beam of electromagnetism is caused to enter said cavity at the first side of said triangular prism along a locus in a plane parallel to said stage plane and at an angle of incidence to a normal to said first side, pass through said first window, then through said liquid/fluid, then through said second window and exit the second side of said triangular prism at an exit angle at least partially determined by the refractive index of said liquid/fluid;
    a trapezoidal prism having a projected apex bisector and first and second sides oriented at angles thereto which meet at a virtual apex; such that in use a beam of electromagnetism is caused to enter said trapazoidal prism at the first side of said triangular prism along a locus in a plane parallel to said stage plane, pass through said trapazoidal prism, and exit the second side thereof at an angle at least partially determined by the refractive index of the material comprising said trapazoidal shaped prism;
    a trapazoidal prism having a projected apex bisector and first and second sides oriented at angles thereto which meet at a virtual apex; there being a cavity within said trapazoidal prism and means for entering liquid/fluid thereinto, said cavity being bounded internally by first and second windows oriented parallel to said first and second sides of said trapazoidal prism respectively; such that in use liquid/fluid is caused to be present in said cavity, and a beam of electromagnetism is caused to enter said cavity at the first side of said trapazoidal prism along a locus in a plane parallel to said stage plane and at an angle of incidence to a normal to said first side, pass through said first window, then through said liquid/fluid, then through said second window and exit the second side of said trapazoidal prism at an exit angle at least partially determined by the refractive index of said liquid/fluid;
  c) assuring that said selected prism is positioned on said rotatable stage such that projected apex bisector of said prism is intersected a projected locus of said the axile means for allowing stage rotation, at one or more distances removed from said apex or virtual apex, said steps being selected from sequences A and B:
    a1) for each of at least two "lateral" positions of said prism on said rotatable stage, which "lateral" positions are offset from one another along a perpendicular to the projected apex bisector of said prism, obtaining data corresponding to a plurality of rotation positions of said stage about said axile means for allowing stage rotation thereabout, said data being obtained by causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles;
    a2) identifying first and second slopes of effective plots of electromagnetic radiation peak intensity vs. angle of incidence of said electromagnetic radiation beam to a normal to the plane of said first side of said prism corresponding to two lateral positions of said prism on said rotatable stage;
    a3) applying said first and second slopes determined in step a2) to calculate "lateral" positioning of said prism along a locus perpendicular to the projected apex bisector of said prism on said rotatable stage to direct the positioning said prism such that its projected apex bisector intersects a projected locus of said the axile means for allowing stage rotation, or to derive a correction factor for application to data obtained with the prism positioned other than with the prism projected apex bisector being intersected a projected locus of said the axile means for allowing stage rotation;
    b1) for one "lateral" position of said prism on said rotatable stage, which "lateral" position is along a perpendicular to the projected apex bisector of said prism, obtaining data corresponding to a plurality of rotation positions of said stage about said axile means for allowing stage rotation thereabout, said data being obtained by causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles;

b2) identifying a slope of an effective plot of electromagnetic radiation peak intensity vs. angle of incidence of said electromagnetic radiation beam to a normal to the plane of said first side of said prism corresponding to said lateral position of said prism on said rotatable stage;

b3) applying said slope determined in step b2) to calculate "lateral" positioning of said prism along a locus perpendicular to the projected apex bisector of said prism on said rotatable stage to direct the positioning said prism such that its projected apex bisector intersects the a projected locus of said the axile means for allowing stage rotation, or to derive a correction factor for application to data obtained with the prism positioned other than with the prism projected apex bisector being intersected a projected locus of said the axile means for allowing stage rotation; and tangibly displaying at least one selection from the group consisting of:

at least some data corresponding to a plurality of rotation positions of said stare about said axile means, obtained in step a1;

at least one effective plot determined in step a2;

obtaining data corresponding to a plurality of rotation positions of said stage about said axile means, obtained in step b1;

the effective plot determined in step b2;

said first or second slope of the effective plot in step a2; and said lateral position factor from step a3 or b3.

11. A method of aligning a system for application in accurately determining the refractive index of material or liquid/fluid which comprises:

a) providing said system which comprises:
 a structure;
 a source of electromagnetic radiation;
 a rotatable stage; and
 a detector;

said rotatable stage having a front side which is defining of a stage plane, and being rotatably mounted to said structure at an axile means for allowing stage rotation thereabout, about which axile means said rotatable stage can be caused to rotate in said stage plane; said source of electromagnetic radiation being fixed in location at an offset from said rotatable stage, and said detector being attached to an arm which is pivotally secured to said structure the location of said rotatable stage;

the relative positioning of said source of electromagnetic radiation, rotatable stage and detector being such that a beam of electromagnetic radiation produced by said source thereof can be directed to proceed in a plane parallel to, but offset from, the stage plane, and enter said detector when it is positioned at a detector pivot angle which allows receipt of said beam of electromagnetic radiation, said pivot angle being effected by pivot motion of said arm which is pivotally secured to said structure the location of said rotatable stage;

b) placing a prism on the front side of said rotatable stage, said prism being a selection from the group consisting of:
 a triangular prism having a projected apex bisector and first and second sides oriented at angles thereto which meet at an apex; such that in use a beam of electromagnetism is caused to enter said triangular shaped prism at the first side thereof along a locus in a plane parallel to said stage plane and at an angle of incidence to a normal to said first side, pass through said triangular shaped prism, and exit the second side of said triangular prism at an exit angle at least partially determined by the refractive index of the material comprising said triangular shaped prism;

a triangular prism having a projected apex bisector and first and second sides oriented at angles thereto which meet at an apex; there being a cavity within said triangular and means for entering liquid/fluid thereinto, said cavity being bounded internally by a first and second windows oriented parallel to said first and second sides of said triangular prism respectively; such that in use liquid/fluid is caused to be present in said cavity, and a beam of electromagnetism is caused to enter said cavity at the first side of said triangular prism along a locus in a plane parallel to said stage plane and at an angle of incidence to a normal to said first side, pass through said first window, then through said liquid/fluid, then through said second window and exit the second side of said triangular prism at an exit angle at least partially determined by the refractive index of said liquid/fluid;

a trapezoidal prism having a projected apex bisector and first and second sides oriented at angles thereto which meet at a virtual apex; such that in use a beam of electromagnetism is caused to enter said trapazoidal prism at the first side of said triangular prism along a locus in a plane parallel to said stage plane, pass through said trapazoidal prism, and exit the second side of said triangular prism at an exit angle at least partially determined by the refractive index of the material comprising said trapazoidal shaped prism;

a trapezoidal prism having a projected apex bisector and first and second sides oriented at angles thereto which meet at a virtual apex; there being a cavity within said trapazoidal prism and means for entering liquid/fluid thereinto, said cavity being bounded internally by first and second windows oriented parallel to said first and second sides of said trapezoidal prism respectively; such that in use liquid/fluid is caused to be present in said cavity, and a beam of electromagnetism is caused to enter said cavity at the first side of said trapazoidal prism along a locus in a plane parallel to said stage plane and at an angle of incidence to a normal to said first side, pass through said first window, then through said liquid/fluid, then through said second window and exit the second side of said trapazoidal prism at an exit angle at least partially determined by the refractive index of said liquid/fluid;

c) assuring that said selected prism is positioned on said rotatable stage such that projected apex bisector of said prism is intersected a projected locus of said the axile means for allowing stage rotation:

a1) for each of a plurality of "lateral" positions of said prism on said rotatable stage, which "lateral" positions are offset from one another along a perpendicular to the projected apex bisector of said prism, obtaining data corresponding to a plurality of rotation positions of said stage about said axile means for allowing stage rotation thereabout, said data being obtained by causing an electromagnetic beam from said source of electromagnetic radiation to enter the first side or first window of said prism at an angle of incidence to a normal to the plane of said first side of said prism, and at each said angle of incidence, obtaining electromagnetic radiation intensity data for each of a plurality of detector position pivot angles such that the detector position pivot angle at which peak electromagnetic radiation intensity is detected is identified;

a2) effectively plotting at least some of said plots of said peak electromagnetic radiation peak intensity data vs. angle of incidence obtained in step a1, on the same set of axes such that the "lateral" offset position of said prism on said rotatable stage associated with the highest electromagnetic radiation peak intensity around the angle of incidence where the effective minimum deviation occurs can be identified, said "lateral" position associated with the highest electromagnetic radiation peak intensity being identifying of the location of whereat the projected apex bisector of said prism is intersected by said projected locus of said the axile means for allowing stage rotation, and applying said information to direct positioning of said prism on said stage rotatable stage so that the prism projected apex bisector intersects a projected locus of said the axile means for allowing stage rotation, or to derive a correction factor for application to data obtained with the prism positioned other than with the prism projected apex bisector being intersected a projected locus of said the axile means for allowing stage rotation; and tangibly displaying at least one selection from the group consisting of:

at least some data corresponding to a plurality of rotation positions of said stage about said axile means, obtained in step a1;

at least one effective Plot determined in step a2;

lateral position or correction factor derived in step a2.

12. A method of improving accuracy in determining the refractive index of material or liquid/fluid can then be described as comprising the steps of:

a) providing a system comprising:
  a structure;
  a source of electromagnetic radiation;
  an rotatable stage; and
  a detector;

said rotatable stage having a front side which is defining of a stage plane, and being rotatably mounted to said structure at an axile means for allowing stage rotation thereabout, about which axile means said rotatable stage can be caused to rotate in said stage plane; said source of electromagnetic radiation being fixed in location at an offset from said rotatable stage, and said detector being attached to an arm which is pivotally secured to said structure the location of said rotatable stage;

the relative positioning of said source of electromagnetic radiation, rotatable stage and detector being such that a beam of electromagnetic radiation produced by said source thereof can be directed to proceed in a plane parallel to, but offset from, the stage plane, and enter said detector when it is positioned at a detector pivot angle which allows receipt of said beam of electromagnetic radiation, said pivot angle being effected by pivot motion of said arm which is pivotally secured to said structure the location of said rotatable stage;

b) placing a prism on the front side of said rotatable stage, said prism being a selection from the group consisting of:

a triangular prism having a projected apex bisector and first and second sides oriented at angles thereto which meet at an apex; such that in use a beam of electromagnetism is caused to enter said triangular shaped prism at the first side thereof along a locus in a plane parallel to said stage plane and at an angle of incidence to a normal to said first side, pass through said triangular shaped prism, and exit the second side of said triangular prism at an exit angle at least partially determined by the refractive index of the material comprising said triangular shaped prism;

a triangular prism having a projected apex bisector and first and second sides oriented at angles thereto which meet at an apex; there being a cavity within said triangular and means for entering liquid/fluid thereinto, said cavity being bounded internally by a first and second windows oriented parallel to said first and second sides of said triangular prism respectively; such that in use liquid/fluid is caused to be present in said cavity, and a beam of electromagnetism is caused to enter said cavity at the first side of said triangular prism along a locus in a plane parallel to said stage plane and at an angle of incidence to a normal to said first side, pass through said first window, then through said liquid/fluid, then through said second window and exit the second side of said triangular prism at an exit angle at least partially determined by the refractive index of said liquid/fluid;

a trapazoidal prism having a projected apex bisector and first and second sides oriented at angles thereto which meet at a virtual apex; such that in use a beam of electromagnetism is caused to enter said trapazoidal prism at the first side of said triangular prism along a locus in a plane parallel to said stage plane, pass through said trapazoidal prism, and exit the second side of said triangular prism at an exit angle at least partially determined by the refractive index of the material comprising said trapazoidal shaped prism;

a trapazoidal prism having a projected apex bisector and first and second sides oriented at angles thereto which meet at a virtual apex; there being a cavity within said trapazoidal prism and means for entering liquid/fluid thereinto, said cavity being bounded internally by first and second windows oriented parallel to said first and second sides of said trapezoidal prism respectively; such that in use liquid/fluid is caused to be present in said cavity, and a beam of electromagnetism is caused to enter said cavity at the first side of said trapazoidal prism along a locus in a plane parallel to said stage plane and at an angle of incidence to a normal to said first side, pass through said first window, then through said liquid/fluid, then through said second window and exit the second side of said trapazoidal prism at an exit angle at least partially determined by the refractive index of said liquid/fluid;

said selected prism being positioned on said rotatable stage such that projected apex bisector thereof is intersected by a projected locus of said the axile means for allowing stage rotation, at a first distance removed from said apex or virtual apex;

c) for each of a plurality of rotation positions of said stage about said axile means for allowing stage rotation thereabout, causing an electromagnetic beam from said source of electromagnetic radiation to enter the first side or first window of said prism at an angle of incidence to a normal to the plane of said first side of said prism, and obtaining electromagnetic radiation intensity data for each of a plurality of detector position pivot angles such that the detector position pivot angle at which peak electromagnetic radiation intensity is detected is identified;

d) providing an effective plot of a deviation angle determined from said detector position pivot angles at which peak electromagnetic radiation peak intensity is present vs. the angle of incidence of said beam of electromagnetic radiation to the normal to said first side of said prism, which plot demonstrates a minimum;

e) in combination with determining the distance from the prism apex at which the projected apex bisector thereof is intersected by a projected locus of said the axile means for allowing stage rotation, utilizing data obtained at the angle of incidence and corresponding minimum deviation angle identified in step d in calculations to determine an accurate index of refraction for the material or liquid/fluid; and tangibly displaying at least one selection from the group consisting of:
    at least some obtained electromagnetic radiation intensity data for each of a plurality of detector position pivot angles in step c;
    the effective plot determined in step d;
    the minimum value of the effective plot demonstrated in step d;
    the accurate index of refraction for the material or liquid/fluid determined in step e.

13. A method of improving accuracy in determining the refractive index of material or liquid/fluid comprising the steps of:
    a) providing a system comprising:
        a structure;
        a source of electromagnetic radiation;
        a stage; and
        a detector;
    said stage having a front side which is defining of a stage plane, and being rotatably mounted to said structure at an axile means for allowing stage rotation thereabout, about which axile means said stage can be caused to rotate in said stage plane; said source of electromagnetic radiation being fixed in location at an offset from said stage, and said detector being attached to an arm which is pivotally secured to said structure the location of said stage;
    the relative positioning of said source of electromagnetic radiation, stage and detector being such that a beam of electromagnetic radiation produced by said source thereof can be directed to proceed in a plane parallel to, but offset from, the stage plane, and enter said detector when it is positioned at a detector pivot angle which allows receipt of said beam of electromagnetic radiation, said pivot angle being effected by pivot motion of said arm which is pivotally secured to said structure the location of said stage;
    b) placing a prism on the front side of said stage, said prism being a selection from the group consisting of:
        a triangular half-prism comprising, as viewed in side elevation, a first side which meets a second side oriented at an angle to said first side, at an apex; there being a cavity within said triangular half-prism and means for entering liquid/fluid thereinto, said cavity being bounded internally by a first window oriented parallel to said first side of said triangular half-prism, a second window oriented parallel to said second side of said triangular half-prism and; such that in use liquid/fluid is caused to be present in said cavity, and a beam of electromagnetism is caused to enter said cavity through said first window at the first side of said triangular half-prism along a locus parallel to said stage plane and perpendicular to said first window, pass sequentially through liquid/fluid and then through said second window and exit the second side of said triangular half-prism at an exit angle at least partially determined by the refractive index of said liquid/fluid;
        a trapazoidal half-prism comprising, as viewed in side elevation, a first side which meets a second side oriented at an angle to said first side, at a virtual apex; there being a cavity within said trapazoidal half-prism and means for entering liquid/fluid thereinto, said cavity being bounded internally by a first window oriented parallel to said first side of said trapezoidal half-prism, a second window oriented parallel to said second side of said trapazoidal half-prism and; such that in use liquid/fluid is caused to be present in said cavity, and a beam of electromagnetism is caused to enter said cavity through said first window at the first side of said trapazoidal half-prism along a locus parallel to said stage plane and perpendicular to said first window, pass sequentially through liquid/fluid and then through said second window and exit the second side of said trapazoidal half-prism at an exit angle at least partially determined by the refractive index of said liquid/fluid;
    c) causing an electromagnetic beam from said source of electromagnetic radiation to enter the first window of said prism at a angle of incidence to a normal, inclusive of normal to the plane of said first side of said prism, and obtaining electromagnetic radiation intensity data for each of a plurality of detector position pivot angles such that the detector position pivot angle at which peak electromagnetic radiation intensity is detected is identified;
    d) utilizing data obtained in calculations to determine an accurate index of refraction for the liquid/fluid; and tangibly displaying at least one selection from the group consisting of:
    at least some obtained electromagnetic radiation intensity data for each of a plurality of detector position pivot angles in step c;
    the accurate index of refraction for the material or liquid/fluid determined in step d.

14. A method as in claim 1 or 2 or 3 or 4 or 5 or 6 or 7 or 10 or 11 or 12 or 13 in which peak values are determined by fitting data with a Mathematical Function which demonstrates a peak, optionally by determining where its First Derivative is Zero and the Second Derivative is Negative.

15. A method as in claim 1 or 2 or 3 or 4 or 5 or 6 or 7 or 10 or 11 or 12 or 13 in which intensity vs. angle of incidence and/or minimum deviation vs. angle of incidence data is modeled by mathematical functions that enable mathematical determination of peak, minimum and/or intersection locations.

16. A method as in claims 2 or 5 or 10 in which more than two slopes of effective plots of electromagnetic radiation peak intensity vs. angle of incidence of said electromagnetic radiation beam to a normal to the plane of said first side of said prism, corresponding to more than two lateral positions of said prism on said rotatable stage are applied to calculate "lateral" positioning of said prism along a locus perpendicular to the projected apex bisector of said prism on said rotatable stage to direct the positioning said prism such that its projected apex bisector intersects a projected locus of said the axile means for allowing stage rotation, or to derive a correction factor for application to data obtained with the prism positioned other than with the prism projected apex bisector being intersected a projected locus of said the axile means for allowing stage rotation.

17. A method as in claims 1 or 2 or 3 or 4 or 5 or 6 or 7 or 8 or 9 or 10 or 11 or 12 or 13 which further comprises the step of determining alignment of said source of electromagnetic radiation and detector by causing electromagnetic radiation from said source thereof to directly pass over, or by, said stage without interacting with said prism or rotatable stage, and enter said detector, and using any offset in alignment to correct determined deviation angle and corresponding refractive index.

18. A method as in claims 1 or 2 or 3 or 4 or 5 or 6 or 7 or 8 or 9 or 10 or 11 or 12 or 13 in which a prism with a cavity is present, which further comprises the step of determining alignment of said source of electromagnetic radiation, said prism and said detector by causing said prism to contain a standard liquid/fluid, and determining the refractive index thereof, comparing the result to known values, and using any deviation from the known values to correct determined refractive index of sample liquid/fluid, and/or correct alignment of said prism.

19. A method as in claims 1 or 2 or 3 or 4 or 5 or 6 or 7 or 8 or 9 or 10 or 11 or 12 in which a prism with a cavity is present, which further comprises the step of determining alignment of said source of electromagnetic radiation, said prism and said detector by causing said prism be empty of all liquid/fluid, determining a baseline, and subtracting said baseline from the data obtained when liquid/fluid is present to further improve accuracy in at least one selection form the group consisting of;
  determining Refractive index; and
  account for any window non-parallelism.

20. A method as in claims 1 or 2 or 3 or 4 or 5 or 6 or 7 or 8 or 9 or 10 or 11 or 12 in which a prism with a cavity is present, which further comprises the step of determining alignment of said source of electromagnetic radiation, said prism and said detector by causing said prism to contain a standard liquid/fluid, and determining the refractive index thereof, comparing said refractive index to known values, and using any deviation from the known values to correct alignment of said source of electromagnetic radiation, said prism and said detector so that said known value of refractive index is obtained, and then utilizing said alignment when investigating a sample liquid/fluid, and/or using any said deviation from known values to correct for measurements of an unknown liquid/fluid.

21. A method as in claims 1 or 2 or 3 or 4 or 5 or 6 or 7 or 8 or 9 or 10 or 11 or 12 or 13 which further comprises determining of the length along the arm which is pivotally secured to said structure at the location of said rotatable stage, at which the detector is located, and/or the length from the apex or virtual apex at which the axis of rotation is located, and including at least one said length in calculations to determine the refractive index of said material or liquid/fluid.

22. A method as in claim 1 which further comprises repeating steps c-e with electromagnetic radiation being caused to proceed through said material or liquid/fluid along a different length pathway corresponding to a different distance of entry into said material or liquid/fluid from said apex or virtual apex, and determining a ratio of corresponding intensities detected in the initial and repeated practice of steps c-e, noting deviation of said ratio from 1.0, and from said deviation determining the absorbence or extinction coefficient of said material or liquid/fluid, in view of known, different, path lengths in said material or liquid/fluid through which said electromagnetic radiation passes in each practice of said steps c-d, and using said deviation to determine the absorption or extinction coefficient of the material or liquid/fluid.

* * * * *